United States Patent
Morrissey

(10) Patent No.: US 11,007,056 B2
(45) Date of Patent: May 18, 2021

(54) PNEUMATICALLY POWER-ASSISTED TAVI DELIVERY SYSTEM

(71) Applicant: St. Jude Medical, Cardiology Division, Inc., St. Paul, MN (US)

(72) Inventor: Michael Shane Morrissey, St. Paul, MN (US)

(73) Assignee: St. Jude Medical, Cardiology Division, Inc., St. Paul, MN (US)

(*) Notice: Subject to any disclaimer, the term of this patent is extended or adjusted under 35 U.S.C. 154(b) by 147 days.

(21) Appl. No.: 16/388,076

(22) Filed: Apr. 18, 2019

(65) Prior Publication Data

US 2019/0240015 A1 Aug. 8, 2019

Related U.S. Application Data

(60) Division of application No. 15/370,342, filed on Dec. 6, 2016, now Pat. No. 10,292,820, which is a continuation of application No. 14/534,575, filed on Nov. 6, 2014, now Pat. No. 9,549,818.

(Continued)

(51) Int. Cl.
*A61F 2/24* (2006.01)
*A61B 17/00* (2006.01)

(52) U.S. Cl.
CPC ...... *A61F 2/2436* (2013.01); *A61B 17/00234* (2013.01); *A61B 2017/00292* (2013.01); *A61B 2017/00544* (2013.01)

(58) Field of Classification Search
CPC .......... A61F 2/2436; A61F 2/95; A61F 2/954; A61F 2/962; A61F 2/966; A61F 2/97;

(Continued)

(56) References Cited

U.S. PATENT DOCUMENTS 3,657,744 A 4/1972 Ersek
4,275,469 A 6/1981 Gabbay
(Continued)

FOREIGN PATENT DOCUMENTS

AU 2011202175 B1 7/2011
DE 19857887 A1 7/2000
(Continued)

OTHER PUBLICATIONS

International Search Report for PCT/US2017/063899, dated Feb. 7, 2018, 3 pages.

(Continued)

*Primary Examiner* — Erich G Herbermann
(74) *Attorney, Agent, or Firm* — Lerner, David, Littenberg, Krumholz & Mentlik, LLP

(57) ABSTRACT

A delivery device for a collapsible prosthetic heart valve may include an operating handle and a catheter assembly. The handle may include a housing, a piston cylinder, a piston longitudinally slidable within the piston cylinder, the piston and the piston cylinder together defining at least one pressure chamber, a deployment actuator coupled to the housing and rotatable relative thereto, and a pneumatic switch adapted to provide a pressurized fluid to the pressure chamber to apply a longitudinal force to the piston. The catheter assembly may include a first shaft around which a valve-receiving compartment is defined, the first shaft being operatively connected to the housing, and a distal sheath operatively connected to the piston, the distal sheath being moveable between a closed condition covering the compartment and an open condition uncovering the compartment. Longitudinal movement of the piston may move the distal sheath between the closed and open conditions.

11 Claims, 5 Drawing Sheets

Related U.S. Application Data

(60) Provisional application No. 61/903,046, filed on Nov. 12, 2013.

(58) Field of Classification Search
CPC ...... A61F 2/2427; A61F 2/243; A61F 2/2439; A61F 2/2451; A61F 2/2454; A61F 2/2457; A61F 2/246; A61F 2/2466; A61B 2017/00292; A61B 2017/00544; A61B 17/000234; A61M 2005/2086; A61M 2005/2026; A61M 5/20; A61M 5/31543; A61M 5/31583
See application file for complete search history.

(56) References Cited

U.S. PATENT DOCUMENTS

| | | | |
|---|---|---|---|
| 4,423,730 A | 1/1984 | Gabbay | |
| 4,491,986 A | 1/1985 | Gabbay | |
| 4,546,767 A * | 10/1985 | Smith | A61B 17/8811 604/224 |
| 4,759,758 A | 7/1988 | Gabbay | |
| 4,922,905 A | 5/1990 | Strecker | |
| 5,391,172 A | 2/1995 | Williams et al. | |
| 5,409,478 A | 4/1995 | Gerry et al. | |
| 5,411,552 A | 5/1995 | Andersen et al. | |
| 5,456,667 A | 10/1995 | Ham et al. | |
| 5,480,423 A | 1/1996 | Ravenscroft et al. | |
| 5,707,376 A | 1/1998 | Kavteladze et al. | |
| 5,843,167 A | 12/1998 | Dwyer et al. | |
| 5,924,424 A | 7/1999 | Stevens et al. | |
| 5,935,163 A | 8/1999 | Gabbay | |
| 5,961,549 A | 10/1999 | Nguyen et al. | |
| 5,968,068 A | 10/1999 | Dehdashtian et al. | |
| 6,077,297 A | 6/2000 | Robinson et al. | |
| 6,083,257 A | 7/2000 | Taylor et al. | |
| 6,090,140 A | 7/2000 | Gabbay | |
| 6,214,036 B1 | 4/2001 | Letendre et al. | |
| 6,264,691 B1 | 7/2001 | Gabbay | |
| 6,267,783 B1 | 7/2001 | Letendre et al. | |
| 6,306,141 B1 | 10/2001 | Jervis | |
| 6,368,348 B1 | 4/2002 | Gabbay | |
| 6,419,695 B1 | 7/2002 | Gabbay | |
| 6,488,702 B1 | 12/2002 | Besselink | |
| 6,514,261 B1 * | 2/2003 | Randall | A61F 2/966 606/108 |
| 6,517,576 B2 | 2/2003 | Gabbay | |
| 6,533,810 B2 | 3/2003 | Hankh et al. | |
| 6,582,464 B2 | 6/2003 | Gabbay | |
| 6,610,088 B1 | 8/2003 | Gabbay | |
| 6,623,518 B2 | 9/2003 | Thompson et al. | |
| 6,685,625 B2 | 2/2004 | Gabbay | |
| 6,719,789 B2 | 4/2004 | Cox | |
| 6,730,118 B2 | 5/2004 | Spenser et al. | |
| 6,736,845 B2 | 5/2004 | Marquez et al. | |
| 6,783,556 B1 | 8/2004 | Gabbay | |
| 6,790,230 B2 | 9/2004 | Beyersdorf et al. | |
| 6,814,746 B2 | 11/2004 | Thompson et al. | |
| 6,830,584 B1 | 12/2004 | Seguin | |
| 6,866,669 B2 | 3/2005 | Buzzard et al. | |
| 6,869,444 B2 | 3/2005 | Gabbay | |
| 6,893,460 B2 | 5/2005 | Spenser et al. | |
| 6,908,481 B2 | 6/2005 | Cribier | |
| 7,018,406 B2 | 3/2006 | Seguin et al. | |
| 7,025,780 B2 | 4/2006 | Gabbay | |
| 7,105,016 B2 | 9/2006 | Shiu et al. | |
| 7,137,184 B2 | 11/2006 | Schreck | |
| 7,160,322 B2 | 1/2007 | Gabbay | |
| 7,247,167 B2 | 7/2007 | Gabbay | |
| 7,267,686 B2 | 9/2007 | DiMatteo et al. | |
| 7,311,730 B2 | 12/2007 | Gabbay | |
| 7,326,236 B2 | 2/2008 | Andreas et al. | |
| 7,329,278 B2 | 2/2008 | Seguin et al. | |
| 7,374,573 B2 | 5/2008 | Gabbay | |
| 7,381,218 B2 | 6/2008 | Schreck | |
| 7,399,315 B2 | 7/2008 | Iobbi | |
| 7,419,501 B2 | 9/2008 | Chiu et al. | |
| 7,452,371 B2 | 11/2008 | Pavcnik et al. | |
| 7,476,244 B2 | 1/2009 | Buzzard et al. | |
| 7,510,572 B2 | 3/2009 | Gabbay | |
| RE40,816 E | 6/2009 | Taylor et al. | |
| 7,585,321 B2 | 9/2009 | Cribier | |
| 7,682,390 B2 | 3/2010 | Seguin | |
| 7,731,742 B2 | 6/2010 | Schlick et al. | |
| 7,803,185 B2 | 9/2010 | Gabbay | |
| 7,846,203 B2 | 12/2010 | Cribier | |
| 7,846,204 B2 | 12/2010 | Letac et al. | |
| 7,914,569 B2 | 3/2011 | Nguyen et al. | |
| 7,967,829 B2 | 6/2011 | Gunderson et al. | |
| 7,993,384 B2 | 8/2011 | Wu et al. | |
| 8,043,353 B2 | 10/2011 | Kaufmann et al. | |
| D648,854 S | 11/2011 | Braido | |
| D652,926 S | 1/2012 | Braido | |
| D652,927 S | 1/2012 | Braido et al. | |
| D653,341 S | 1/2012 | Braido et al. | |
| D653,342 S | 1/2012 | Braido et al. | |
| D653,343 S | 1/2012 | Ness et al. | |
| D654,169 S | 2/2012 | Braido | |
| D654,170 S | 2/2012 | Braido et al. | |
| 8,353,955 B2 | 1/2013 | Styrc et al. | |
| 8,562,663 B2 | 10/2013 | Mearns et al. | |
| 8,568,475 B2 | 10/2013 | Nguyen et al. | |
| 8,778,019 B2 | 7/2014 | Knippel et al. | |
| 8,790,386 B2 | 7/2014 | Dwork | |
| 8,814,931 B2 | 8/2014 | Wang et al. | |
| 9,060,860 B2 | 6/2015 | Morris et al. | |
| 9,675,485 B2 | 6/2017 | Essinger et al. | |
| 9,820,877 B2 | 11/2017 | Cummins | |
| 9,867,701 B2 | 1/2018 | Morris et al. | |
| 9,883,960 B2 | 2/2018 | Cummins et al. | |
| 9,974,376 B1 | 5/2018 | Liu | |
| 10,064,748 B2 | 9/2018 | Shimoyama | |
| 10,213,299 B2 | 2/2019 | Backus et al. | |
| 10,292,820 B2 | 5/2019 | Morrissey | |
| 2002/0036220 A1 | 3/2002 | Gabbay | |
| 2002/0183827 A1 | 12/2002 | Derus et al. | |
| 2003/0050694 A1 | 3/2003 | Yang et al. | |
| 2003/0130726 A1 | 7/2003 | Thorpe et al. | |
| 2003/0144725 A1 | 7/2003 | Lombardi | |
| 2003/0191516 A1 | 10/2003 | Weldon et al. | |
| 2004/0039436 A1 | 2/2004 | Spenser et al. | |
| 2004/0049262 A1 | 3/2004 | Obermiller et al. | |
| 2004/0093075 A1 | 5/2004 | Kuehne | |
| 2004/0148009 A1 | 7/2004 | Buzzard et al. | |
| 2004/0186563 A1 | 9/2004 | Lobbi | |
| 2004/0210304 A1 | 10/2004 | Seguin et al. | |
| 2004/0260390 A1 | 12/2004 | Sarac et al. | |
| 2005/0004583 A1 | 1/2005 | Oz et al. | |
| 2005/0027305 A1 | 2/2005 | Shiu et al. | |
| 2005/0049667 A1 | 3/2005 | Arbefeuille et al. | |
| 2005/0080476 A1 | 4/2005 | Gunderson et al. | |
| 2005/0096726 A1 | 5/2005 | Sequin et al. | |
| 2005/0137695 A1 | 6/2005 | Salahieh et al. | |
| 2005/0137697 A1 | 6/2005 | Salahieh et al. | |
| 2005/0149159 A1 | 7/2005 | Andreas et al. | |
| 2005/0240254 A1 | 10/2005 | Austin | |
| 2005/0256566 A1 | 11/2005 | Gabbay | |
| 2006/0008497 A1 | 1/2006 | Gabbay | |
| 2006/0074484 A1 | 4/2006 | Huber | |
| 2006/0106415 A1 | 5/2006 | Gabbay | |
| 2006/0122692 A1 | 6/2006 | Gilad et al. | |
| 2006/0142848 A1 | 6/2006 | Gabbay | |
| 2006/0167468 A1 | 7/2006 | Gabbay | |
| 2006/0173532 A1 | 8/2006 | Flagle et al. | |
| 2006/0206202 A1 | 9/2006 | Bonhoeffer et al. | |
| 2006/0241744 A1 | 10/2006 | Beith | |
| 2006/0259120 A1 | 11/2006 | Vongphakdy et al. | |
| 2006/0259136 A1 | 11/2006 | Nguyen et al. | |
| 2006/0259137 A1 | 11/2006 | Artof et al. | |
| 2006/0265056 A1 | 11/2006 | Nguyen et al. | |
| 2006/0276813 A1 | 12/2006 | Greenberg | |
| 2006/0282150 A1 | 12/2006 | Olson et al. | |
| 2006/0282157 A1 | 12/2006 | Hill et al. | |
| 2007/0010876 A1 | 1/2007 | Salahieh et al. | |

(56) References Cited

U.S. PATENT DOCUMENTS

| | | |
|---|---|---|
| 2007/0027534 A1 | 2/2007 | Bergheim et al. |
| 2007/0043435 A1 | 2/2007 | Seguin et al. |
| 2007/0055358 A1 | 3/2007 | Krolik et al. |
| 2007/0067029 A1 | 3/2007 | Gabbay |
| 2007/0073391 A1 | 3/2007 | Bourang et al. |
| 2007/0088431 A1 | 4/2007 | Bourang et al. |
| 2007/0093890 A1 | 4/2007 | Eliasen et al. |
| 2007/0100435 A1 | 5/2007 | Case et al. |
| 2007/0112422 A1 | 5/2007 | Dehdashtian |
| 2007/0156225 A1 | 7/2007 | George et al. |
| 2007/0162100 A1 | 7/2007 | Gabbay |
| 2007/0168013 A1 | 7/2007 | Douglas |
| 2007/0203575 A1 | 8/2007 | Forster et al. |
| 2007/0213813 A1 | 9/2007 | Von Segesser et al. |
| 2007/0239271 A1 | 10/2007 | Nguyen |
| 2007/0244545 A1 | 10/2007 | Birdsall et al. |
| 2007/0244552 A1 | 10/2007 | Salahieh et al. |
| 2007/0260301 A1 | 11/2007 | Chuter et al. |
| 2007/0288087 A1 | 12/2007 | Fearnot et al. |
| 2008/0004688 A1 | 1/2008 | Spenser et al. |
| 2008/0009940 A1 | 1/2008 | Cribier |
| 2008/0021552 A1 | 1/2008 | Gabbay |
| 2008/0039934 A1 | 2/2008 | Styrc |
| 2008/0071369 A1 | 3/2008 | Tuval et al. |
| 2008/0082159 A1 | 4/2008 | Tseng et al. |
| 2008/0097595 A1 | 4/2008 | Gabbay |
| 2008/0114452 A1 | 5/2008 | Gabbay |
| 2008/0125853 A1 | 5/2008 | Bailey et al. |
| 2008/0140189 A1 | 6/2008 | Nguyen et al. |
| 2008/0147179 A1 | 6/2008 | Cai et al. |
| 2008/0147182 A1 | 6/2008 | Righini et al. |
| 2008/0147183 A1 | 6/2008 | Styrc |
| 2008/0154355 A1 | 6/2008 | Benichou et al. |
| 2008/0154356 A1 | 6/2008 | Obermiller et al. |
| 2008/0228264 A1 | 9/2008 | Li et al. |
| 2008/0243245 A1 | 10/2008 | Thambar et al. |
| 2008/0255662 A1 | 10/2008 | Stacchino et al. |
| 2008/0262602 A1 | 10/2008 | Wilk et al. |
| 2008/0269878 A1 | 10/2008 | Iobbi |
| 2008/0269879 A1 | 10/2008 | Sathe et al. |
| 2009/0024137 A1 | 1/2009 | Chuter et al. |
| 2009/0054975 A1 | 2/2009 | del Nido et al. |
| 2009/0105798 A1 | 4/2009 | Koch |
| 2009/0112309 A1 | 4/2009 | Jaramillo et al. |
| 2009/0118826 A1 | 5/2009 | Khaghani |
| 2009/0138079 A1 | 5/2009 | Tuval et al. |
| 2009/0287299 A1 | 11/2009 | Tabor et al. |
| 2010/0004740 A1 | 1/2010 | Seguin et al. |
| 2010/0036484 A1 | 2/2010 | Hariton et al. |
| 2010/0049306 A1 | 2/2010 | House et al. |
| 2010/0049313 A1 | 2/2010 | Alon et al. |
| 2010/0082094 A1 | 4/2010 | Quadri et al. |
| 2010/0087907 A1 | 4/2010 | Lattouf |
| 2010/0114305 A1 | 5/2010 | Kang et al. |
| 2010/0121434 A1 | 5/2010 | Paul et al. |
| 2010/0131055 A1 | 5/2010 | Case et al. |
| 2010/0168778 A1 | 7/2010 | Braido |
| 2010/0168839 A1 | 7/2010 | Braido et al. |
| 2010/0174290 A1 | 7/2010 | Wuebbeling et al. |
| 2010/0185277 A1 | 7/2010 | Braido et al. |
| 2010/0191326 A1 | 7/2010 | Alkhatib |
| 2010/0204781 A1 | 8/2010 | Alkhatib |
| 2010/0204785 A1 | 8/2010 | Alkhatib |
| 2010/0217382 A1 | 8/2010 | Chau et al. |
| 2010/0249911 A1 | 9/2010 | Alkhatib |
| 2010/0249923 A1 | 9/2010 | Alkhatib et al. |
| 2010/0286768 A1 | 11/2010 | Alkhatib |
| 2010/0298931 A1 | 11/2010 | Quadri et al. |
| 2011/0029072 A1 | 2/2011 | Gabbay |
| 2011/0208298 A1 | 8/2011 | Tuval et al. |
| 2011/0224678 A1 | 9/2011 | Gabbay |
| 2011/0282425 A1 | 11/2011 | Dwork |
| 2011/0288626 A1 | 11/2011 | Straubinger et al. |
| 2011/0295216 A1 | 12/2011 | Miller |
| 2012/0022635 A1 | 1/2012 | Yamashita |
| 2012/0053574 A1 | 3/2012 | Murray, III et al. |
| 2012/0078352 A1 | 3/2012 | Wang et al. |
| 2012/0197391 A1 | 8/2012 | Alkhatib et al. |
| 2012/0310332 A1 | 12/2012 | Murray et al. |
| 2013/0030520 A1 | 1/2013 | Lee et al. |
| 2013/0131774 A1 | 5/2013 | Nabulsi et al. |
| 2013/0138118 A1 | 5/2013 | Doyle |
| 2013/0231735 A1 | 9/2013 | Deem et al. |
| 2013/0297011 A1 | 11/2013 | Morris et al. |
| 2013/0304179 A1 | 11/2013 | Bialas et al. |
| 2014/0067050 A1 | 3/2014 | Costello et al. |
| 2014/0135909 A1* | 5/2014 | Carr .............. A61F 2/2427 623/2.11 |
| 2014/0343670 A1 | 11/2014 | Bakis et al. |
| 2015/0305867 A1 | 10/2015 | Liu et al. |
| 2017/0056169 A1 | 3/2017 | Johnson et al. |

FOREIGN PATENT DOCUMENTS

| | | |
|---|---|---|
| DE | 20000659 U1 | 5/2001 |
| DE | 10121210 A1 | 11/2002 |
| DE | 202008009610 U1 | 12/2008 |
| EP | 0850607 A1 | 7/1998 |
| EP | 1000590 A1 | 5/2000 |
| EP | 1129744 A1 | 9/2001 |
| EP | 1157673 A2 | 11/2001 |
| EP | 1360942 A1 | 11/2003 |
| EP | 1584306 A1 | 10/2005 |
| EP | 1598031 A2 | 11/2005 |
| FR | 2847800 B1 | 10/2005 |
| JP | 2001504717 A | 4/2001 |
| JP | 2003334254 A | 11/2003 |
| JP | 2004130074 | 4/2004 |
| JP | 2010504820 A | 2/2010 |
| JP | 2010526609 A | 8/2010 |
| JP | 2010531193 | 9/2010 |
| JP | 2012500665 A | 1/2012 |
| WO | 9117720 A1 | 11/1991 |
| WO | 9716133 A1 | 8/1997 |
| WO | 9832412 A2 | 7/1998 |
| WO | 9913801 A1 | 3/1999 |
| WO | 0018330 A1 | 4/2000 |
| WO | 0069368 A2 | 11/2000 |
| WO | 0128259 A1 | 4/2001 |
| WO | 0149213 A2 | 7/2001 |
| WO | 0154625 A1 | 8/2001 |
| WO | 0156500 A2 | 8/2001 |
| WO | 0176510 A2 | 10/2001 |
| WO | 0236048 A1 | 5/2002 |
| WO | 0247575 A2 | 6/2002 |
| WO | 03047468 A1 | 6/2003 |
| WO | 06073626 A2 | 7/2006 |
| WO | 07071436 A2 | 6/2007 |
| WO | 2008042266 A2 | 4/2008 |
| WO | 08070797 A2 | 6/2008 |
| WO | 2008138584 A1 | 11/2008 |
| WO | 2009001309 | 12/2008 |
| WO | 2009011866 A1 | 1/2009 |
| WO | 2009029199 A1 | 3/2009 |
| WO | 2009042196 A2 | 4/2009 |
| WO | 2009091509 A1 | 7/2009 |
| WO | 2010008548 A2 | 1/2010 |
| WO | 2010008549 A1 | 1/2010 |
| WO | 2010051025 A1 | 5/2010 |
| WO | 2010087975 A1 | 8/2010 |
| WO | 2010096176 A1 | 8/2010 |
| WO | 2010098857 A1 | 9/2010 |
| WO | 2011134531 A9 | 11/2011 |
| WO | 2012026965 A2 | 3/2012 |
| WO | 2012027487 A2 | 3/2012 |
| WO | 2012036741 A2 | 3/2012 |
| WO | 2016059084 A2 | 4/2016 |

OTHER PUBLICATIONS

International Search Report Application No. PCT/US2011/048963, dated Dec. 15, 2011.

(56) References Cited

OTHER PUBLICATIONS

International Search Report Application No. PCT/US2011/048989, dated Dec. 15, 2011.
International Search Report Application No. PCT/US2011/048967, dated Dec. 15, 2011.
Ruiz, Carlos, Overview of PRE-CE Mark Transcatheter Aortic Valve Technologies, Euro PCR—dated May 25, 2010.
International Search Report and Written Opinion for Application No. PCT/US2011/001615 dated Jul. 11, 2012.
Alkhatib, U.S. Appl. No. 13/216,124, filed Aug. 23, 2011, titled "Leaflet Suturing to Commissure Points for Prosthetic Heart Valve".
International Search Report for Application No. PCT/US2011/001597 dated Mar. 7, 2012.
Knippel, U.S. Appl. No. 13/234,782, filed Sep. 16, 2011, titled "Staged Deployment Devices and Method for Transcatheter Heart Valve Delivery".
Morris, U.S. Appl. No. 13/788,820, filed Mar. 7, 2013, titled "Devices and Methods for Transcatheter Heart Valve Delivery".
Wang, U.S. Appl. No. 13/212,442, filed Aug. 18, 2011, titled "Staged Deployment Devices and Methods for Transcatheter Heart Valve Delivery Systems".
Australian Examination Report for Application No. 2011293898 dated Jul. 26, 2013.
International Search Report and Written Opinion for Application No. PCT/US2013/039407 dated Feb. 10, 2014.
International Search Report and Written Opinion for Application No. PCT/US2011/001450 dated Mar. 5, 2012.
International Search Report and Written Opinion for Application No. PCT/US2014/064253 dated Feb. 3, 2015.
Japanese Office Action for Application No. 2013-525891 dated May 8, 2015.
Extended European Search Report for Application No. 16196712 dated May 9, 2017.
International Search Report for Application No. PCT/US2011/001615 dated Jul. 11, 2012.
International Search Report from PCT/US2017/063893, dated Feb. 7, 2018, 3 pages.
International Search Report and Written Opinion for PCT/US2018/031973, dated Oct. 19, 2018.

\* cited by examiner

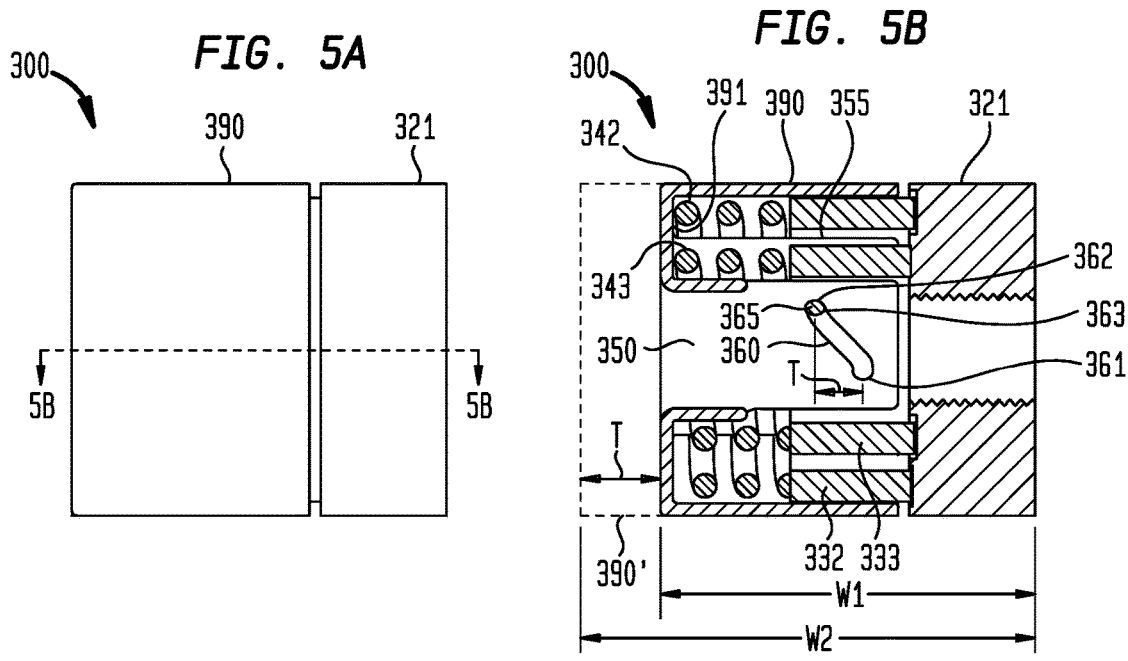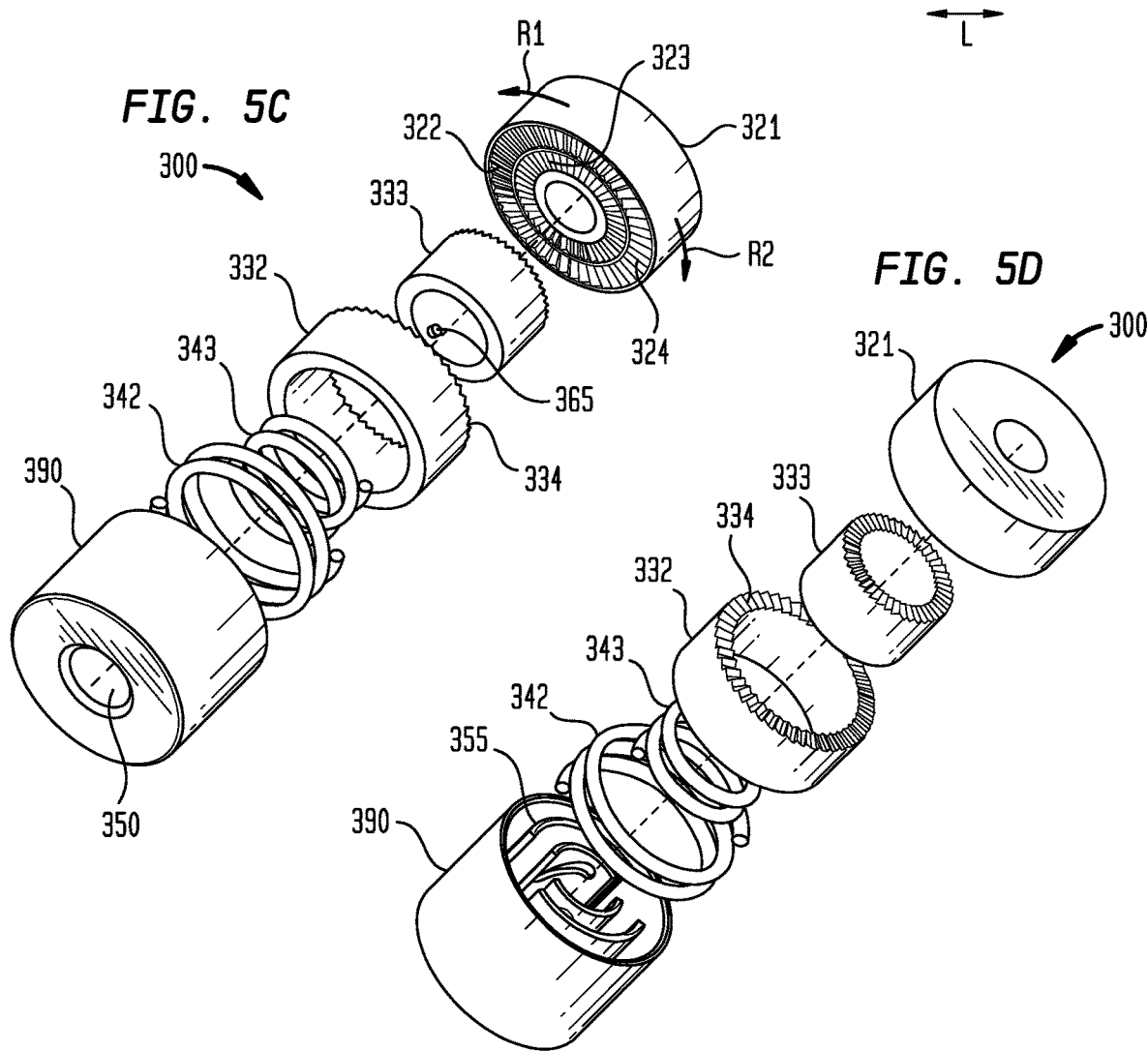

PNEUMATICALLY POWER-ASSISTED TAVI DELIVERY SYSTEM

CROSS-REFERENCE TO RELATED APPLICATION

The present application is a divisional of U.S. patent application Ser. No. 15/370,342, filed Dec. 6, 2016, which is a continuation of U.S. patent application Ser. No. 14/534,575, filed Nov. 6, 2014, now U.S. Pat. No. 9,549,818, which claims the benefit of the filing date of U.S. Provisional Patent Application No. 61/903,046, filed Nov. 12, 2013, the disclosures of all of which are hereby incorporated herein by reference.

BACKGROUND OF THE INVENTION

The present invention is related to prosthetic heart valve replacement, and more particularly to devices, systems, and methods for transapical and transcatheter delivery of collapsible prosthetic heart valves.

Prosthetic heart valves that are collapsible to a relatively small circumferential size can be delivered into a patient less invasively than valves that are not collapsible. For example, a collapsible valve may be delivered into a patient via a tube-like delivery apparatus such as a catheter, a trocar, a laparoscopic instrument, or the like. This collapsibility can avoid the need for a more invasive procedure such as full open-chest, open-heart surgery.

Collapsible prosthetic heart valves typically take the form of a valve structure mounted on a stent. There are two types of stents on which the valve structures are ordinarily mounted: a self-expanding stent and a balloon-expandable stent. To place such valves into a delivery apparatus and ultimately into a patient, the valve must first be collapsed or crimped to reduce its circumferential size.

When a collapsed prosthetic valve has reached the desired implant site in the patient (e.g., at or near the annulus of the patient's heart valve that is to be replaced by the prosthetic valve), the prosthetic valve can be deployed or released from the delivery apparatus and re-expanded to full operating size. For balloon-expandable valves, this generally involves releasing the entire valve, assuring its proper location, and then expanding a balloon positioned within the valve stent. For self-expanding valves, on the other hand, the stent automatically expands as the sheath covering the valve is withdrawn.

BRIEF SUMMARY OF THE INVENTION

Delivery devices for a collapsible prosthetic heart valve and methods of delivering a collapsible prosthetic heart valve using same are aspects of the invention. In addition, any device having one or more of the following features and used in the transcatheter delivery of a collapsible heart valve are the specific aspects of the invention.

A delivery device for a collapsible prosthetic heart valve may include an operating handle and a catheter assembly. The operating handle may include a housing defining a movement space therein, a piston cylinder disposed within the movement space, a piston slidable in a longitudinal direction within the piston cylinder, the piston and the piston cylinder together defining at least one pressure chamber, a deployment actuator coupled to the housing and rotatable relative to the housing, and a pneumatic switch in fluid communication with the pressure chamber, the pneumatic switch adapted to provide a pressurized fluid to the pressure chamber to apply a force to the piston in the longitudinal direction.

The catheter assembly may include a first shaft around which a compartment is defined, the first shaft being operatively connected to the housing, the compartment being adapted to receive the valve in an assembled condition, and a distal sheath operatively connected to the piston, the distal sheath being moveable between a closed condition covering the compartment and an open condition uncovering the compartment for deployment of the valve. Movement of the piston in the longitudinal direction in the piston cylinder may move the distal sheath between the closed condition and the open condition.

The piston cylinder may include a proximal piston cylinder and a distal piston cylinder, the piston and the proximal piston cylinder together defining a proximal pressure chamber and the piston and the distal piston cylinder together defining a distal pressure chamber. The first shaft may be attached to the distal sheath and operatively connected to the piston, the catheter assembly also including an outer shaft connecting the housing to the compartment and at least partially surrounding the first shaft. The piston cylinder may be a distal piston cylinder surrounding a distal end of the piston. The catheter assembly may also include an outer shaft attached to the distal sheath and operatively connected to the piston, the outer shaft at least partially surrounding the first shaft. The piston cylinder may be a proximal piston cylinder surrounding a proximal end of the piston.

The deployment actuator may be a knob rotatable about a central axis that extends parallel to the longitudinal direction. Rotation of the deployment actuator in a first direction may move the piston proximally in the longitudinal direction, and rotation of the deployment actuator in a second direction opposite the first direction may move the piston distally in the longitudinal direction. The piston may be a threaded rod in threaded engagement with the deployment actuator.

The operating handle may also include a coupling assembly rotationally fixed to the deployment actuator, the coupling assembly having an engaged position in which rotation of the deployment actuator moves the threaded rod in the longitudinal direction, and a disengaged position in which rotation of the deployment actuator does not move the threaded rod in the longitudinal direction. The coupling assembly may include a split nut having a plurality of threaded split nut portions, the split nut portions each being linearly slidable away from one another and away from the threaded rod, the split nut having an engaged position in which threads of the split nut portions are engaged with the threaded rod and a disengaged position in which the threads of the split nut portions do not engage the threaded rod.

Rotation of the deployment actuator in a first direction may actuate the pneumatic switch and may provide the pressurized fluid to the pressure chamber. The operating handle may also include a toggle guide moveable in the longitudinal direction relative to the deployment actuator, and rotation of the deployment actuator in the first direction may cause movement of the toggle guide in the longitudinal direction away from the deployment actuator, thereby actuating the pneumatic switch.

The piston cylinder may include a proximal piston cylinder and a distal piston cylinder, the piston and the proximal piston cylinder together defining a proximal pressure chamber and the piston and the distal piston cylinder together defining a distal pressure chamber. Rotation of the deployment actuator in a first direction may actuate the pneumatic switch and may provide the pressurized fluid to the proximal pressure chamber, and rotation of the deployment actuator in a second direction opposite the first direction may actuate the pneumatic switch and may provide the pressurized fluid to the distal pressure chamber.

A method of delivering a collapsible prosthetic heart valve in a patient may include providing a delivery device having a catheter assembly and an operating handle, the catheter assembly including a compartment adapted to receive the valve in an assembled condition, the operating handle including a housing defining a movement space therein, a piston cylinder disposed within the movement space, a piston slidable in first and second longitudinal directions within the piston cylinder, the piston and the piston cylinder together defining at least one pressure chamber, a deployment actuator coupled to the housing and rotatable relative to the housing, and a pneumatic switch in fluid communication with the pressure chamber.

The method may also include loading the valve into the compartment of the catheter assembly and covering the compartment and the valve with a distal sheath of the catheter assembly, and inserting the catheter assembly into the patient so that the valve is positioned at a target location within the patient. The method may further include actuating the pneumatic switch, thereby providing a pressurized fluid to the pressure chamber and applying a force to the piston in the first longitudinal direction, and opening or closing the compartment by rotating the deployment actuator to move the piston of the operating handle in the first longitudinal direction.

The piston cylinder may include a proximal piston cylinder and a distal piston cylinder, the piston and the proximal piston cylinder together defining a proximal pressure chamber and the piston and the distal piston cylinder together defining a distal pressure chamber. The step of opening or closing the compartment may include opening the compartment by rotating the deployment actuator in a first rotational direction to move the piston of the operating handle in the first longitudinal direction. The method may also include actuating the pneumatic switch, thereby providing a pressurized fluid to the distal chamber and applying a force to the piston in the second longitudinal direction, and closing the compartment by rotating the deployment actuator in a second rotational direction to move the piston of the operating handle in the second longitudinal direction.

The catheter assembly may also include a first shaft around which the compartment is defined and an outer shaft connecting the housing to the compartment and at least partially surrounding the first shaft. The first shaft and the distal sheath may be operatively connected to the piston, the piston cylinder may be a distal piston cylinder surrounding a distal end of the piston, and the step of actuating the pneumatic switch may provide a pressurized fluid to the pressure chamber and may apply a force to the piston in the second longitudinal direction.

The catheter assembly may also include a first shaft around which the compartment is defined and an outer shaft connecting the carriage assembly to the distal sheath and at least partially surrounding the first shaft. The first shaft may be fixedly connected to the housing, the distal sheath may be operatively connected to the piston, the piston cylinder may be a proximal piston cylinder surrounding a proximal end of the piston, and the step of actuating the pneumatic switch may provide a pressurized fluid to the pressure chamber and may apply a force to the piston in the first longitudinal direction.

The deployment actuator may be a knob rotatable about a central axis that extends parallel to the first and second longitudinal directions. The piston may be a threaded rod in threaded engagement with the deployment actuator, and the deployment actuator may be longitudinally constrained relative to the housing. The actuating of the pneumatic switch to provide the pressurized fluid to the pressure chamber may be effected by the rotation of the deployment actuator in the first rotational direction.

The operating handle may also include a toggle guide moveable in the first and second longitudinal directions relative to the deployment actuator. The rotation of the deployment actuator in the first rotational direction may cause movement of the toggle guide in the first longitudinal direction away from the deployment actuator, thereby effecting the actuating of the pneumatic switch. The target location may be the native aortic annulus of the patient. The inserting step may include inserting the distal sheath of the catheter assembly through the apex of the heart of the patient. The inserting step may include inserting the distal sheath of the catheter assembly through a femoral artery of the patient.

BRIEF DESCRIPTION OF THE DRAWINGS

Various embodiments of the present invention will now be described with reference to the appended drawings. It is to be appreciated that these drawings depict only some embodiments of the invention and are therefore not to be considered limiting of its scope.

FIG. 5A is a side view of a smart wheel assembly that can be integrated into the operating handle of FIG. 1A or FIG. 3A;

FIG. 5B is a longitudinal cross-section of the smart wheel assembly of FIG. 5A; and FIGS. 5C and 5D are exploded perspective views of the smart wheel assembly of FIG. 5A.

DETAILED DESCRIPTION

There is a need for further improvements to the devices, systems, and methods for transcatheter delivery of collapsible prosthetic heart valves, and in particular, self-expanding prosthetic heart valves.

Embodiments of the present invention may include an operating handle having proximal and distal pressure chambers that are adapted to provide either a distal or proximal force assist during deployment of a prosthetic valve, such that the amount of force required of a user to rotate a deployment actuator knob of the operating handle is reduced, particularly during resheathing of a prosthetic valve after it has been partially expanded in a patient, which is typically resisted by significant friction (e.g., 6-20 lbs.) between a distal sheath and the prosthetic valve. In some embodiments, the operating handles described herein may provide 8-10 lbs. of distal or proximal force assist in the longitudinal direction of the handle.

As used herein, the terms "proximal" and "distal" are to be taken as relative to a user using the disclosed delivery devices. "Proximal" is to be understood as relatively close to the user and "distal" is to be understood as relatively farther away from the user. Also as used herein, the terms "generally," "substantially," and "about" are intended to mean that slight deviations from absolute are included within the scope of the term so modified.

Figure 1A:
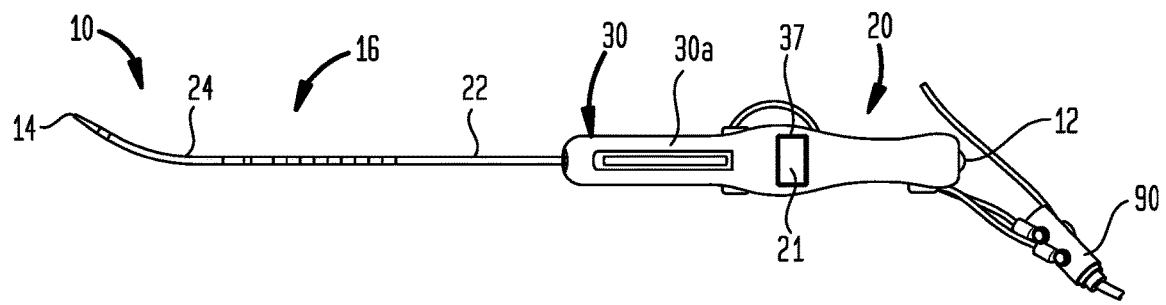
FIG. 1A is a top view of a transapical delivery device for a collapsible prosthetic heart valve.
Figure 1B:
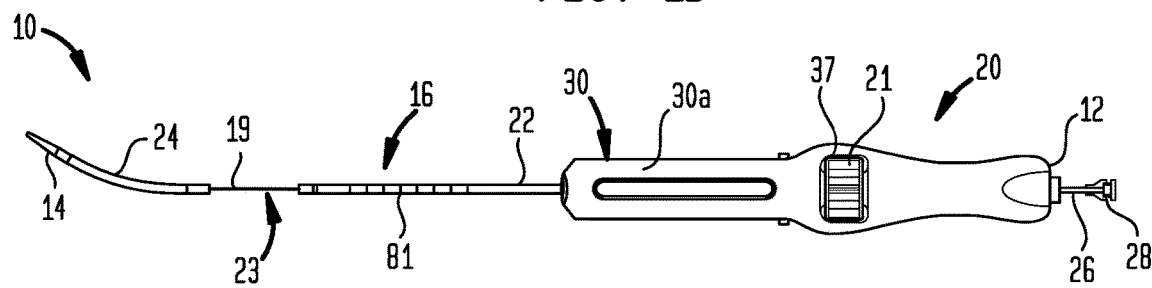
FIG. 1B is a top view of the delivery device FIG. 1A, shown with the compartment unsheathed.
Figure 1C:
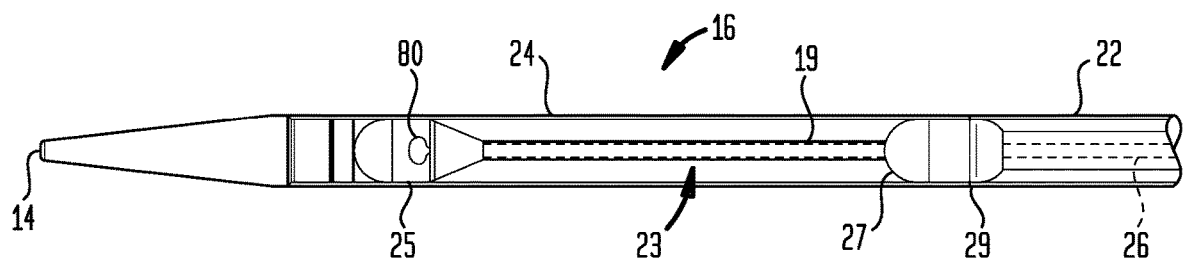
FIG. 1C is a partial longitudinal cross-section of the distal portion of the catheter assembly of FIG. 1A.

Referring now to FIGS. 1A-1C to illustrate the structure and function of the present invention, an exemplary transapical delivery device 10 for a collapsible prosthetic heart valve (or other types of self-expanding collapsible stents) has a catheter assembly 16 for delivering the heart valve to and deploying the heart valve at a target location, and an operating handle 20 for controlling deployment of the valve from the catheter assembly. The delivery device 10 extends from a proximal end 12 to an atraumatic tip 14 at the distal end of the catheter assembly 16. The atraumatic tip 14 may be formed from or may include a radiopaque material to enable the tip to be visible under fluoroscopy during a deployment procedure.

The catheter assembly 16 is adapted to receive a collapsible prosthetic heart valve (not shown) in a compartment 23 defined between a tubular support shaft 19 and a distal sheath 24 that surrounds the support shaft. The support shaft 19 is fixedly coupled to the operating handle 20 by an outer shaft 22, the proximal end of which is fixedly connected to the operating handle and the distal end of which is fixedly connected to the support shaft. The distal sheath 24 is fixedly coupled to an inner shaft 26 by the atraumatic tip 14. The inner shaft 26 extends from the autraumatic tip 14 through the support shaft 19 and through the operating handle 20. The distal sheath 24, atraumatic tip 14, and inner shaft 26 are together slidable relative to the support shaft 19, outer shaft 22, and operating handle 20, such that the distal sheath can selectively cover or uncover the compartment 23. The connection of the distal sheath 24 to the atraumatic tip 14 thus enables the inner shaft 26 to control the movement of the distal sheath both proximally and distally.

The support shaft 19 extends between a pair of spaced retainers 25 and 27 affixed thereto and defining the ends of the compartment 23. A collapsible prosthetic valve may be assembled around the support shaft 19 and between the retainers 25 and 27 in the compartment 23. The retainer 25 may have recesses 80 therein that are adapted to hold corresponding retention members of the valve.

The distal sheath 24 is affixed at its distal end to the atraumatic tip 14, and its proximal end 29 terminates at or near the retainer 27 when the distal sheath is fully covering the compartment 23, as shown in FIG. 1C. The distal end of the outer shaft 22 terminates at or near the retainer 27 and preferably abuts the proximal end 29 of the distal sheath 24 when the distal sheath is in the proximalmost position, as shown in FIG. 1C. The proximal end 29 of the distal sheath 24 is spaced apart from the retainer 27 when the compartment 23 is at least partially uncovered, as shown in FIG. 1B.

The delivery device 10 may include measurement markings 81 (FIG. 1B) thereon to assist the user in determining the location or depth of portions of the device with respect to the aortic annulus or the apex of the heart. One or more of the markings 81 may be located on the distal sheath 24, so that the user can determine how far the distal sheath has moved relative to its initial position during deployment of a valve. One or more of the markings 81 may be located on the support shaft 19 at the anticipated location of the leaflets of the prosthetic aortic valve, so that the user can know where the leaflets are relative to the native aortic annulus during deployment of the valve. One or more of the markings 81 may be located on the outer shaft 22, so that the user can determine how far the atraumatic tip 14 has been inserted into a patient before uncovering of the compartment 23 has begun. Each of the measurement markings 81 may include a material selected from the group consisting of a polymer, gold, platinum, nitinol, and combinations thereof, or one or more other metallic or polymer materials, and such markings may be radiopaque, i.e., the markings may be visible to the user under fluoroscopy.

The operating handle 20 is adapted to control deployment of a prosthetic valve located in the compartment 23 by permitting a user to selectively slide the inner shaft 26 and the attached distal sheath 24 distally or proximally relative to the support shaft 19, thereby respectively uncovering or covering the compartment with the distal sheath.

Figure 2A:
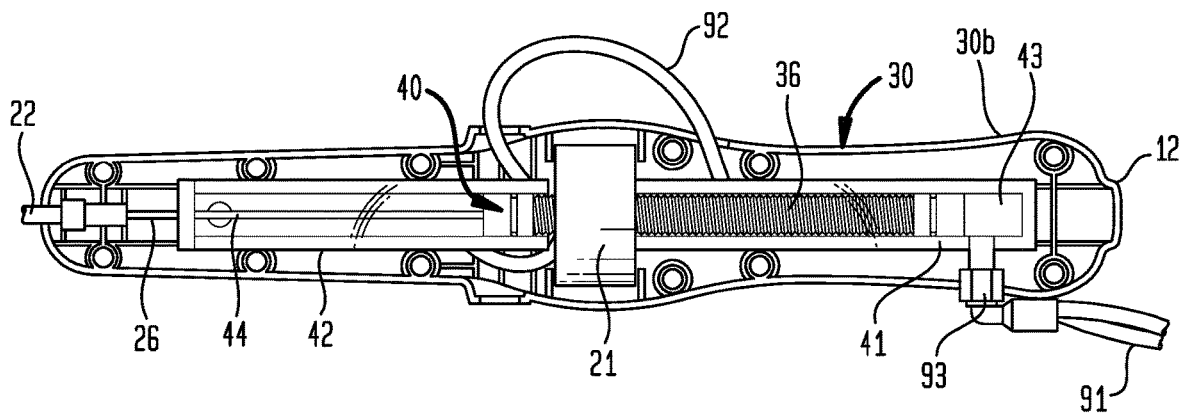
FIG. 2A is a top view of the operating handle of FIG. 1A with the housing partially removed to show the interior thereof.
Figure 2B:
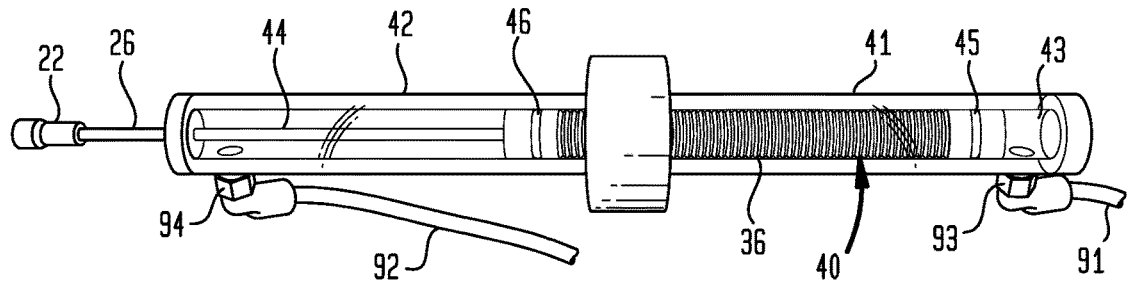
FIG. 2B is a top view of the piston assembly of FIG. 2A.
Figure 2C:
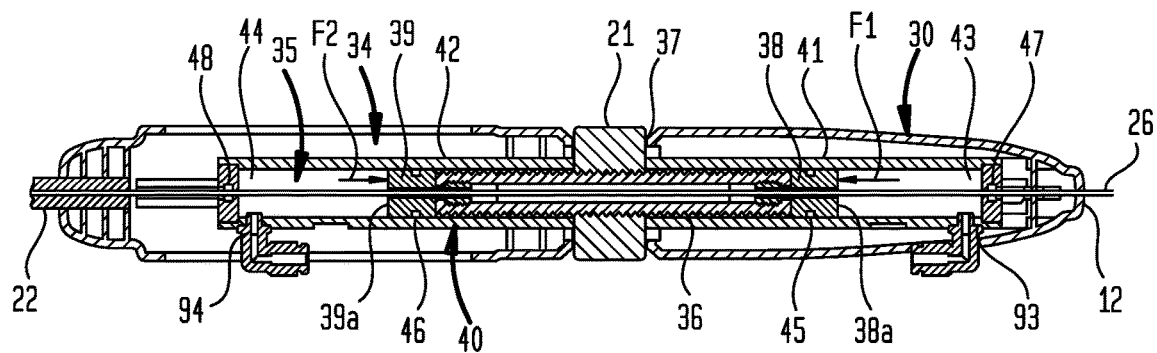
FIG. 2C is a longitudinal cross-section of the operating handle of FIG. 1A.

Referring to FIGS. 2A-2C, the proximal end of the outer shaft 22 is connected in substantially fixed relationship to an outer housing 30 of the operating handle 20, and a location near the proximal end of the inner shaft 26 is fixedly connected to a piston in the form of a threaded rod 36 that is translatable along a longitudinal axis of the handle housing. As a result of the structure, a user can selectively slide the inner shaft 26 relative to the outer shaft 22 by translating the threaded rod 36 relative to the housing 30. The threaded rod 36 has an unthreaded proximal end 38 with an end surface 38a, and an unthreaded distal end 39 with an end surface 39a. The threaded rod 36 preferably is longer than the anticipated maximum travel distance of the distal sheath 24 (e.g., at least about 50 mm), such that the threaded rod 36 does not fully disengage from the deployment actuator 21 (described below) during unsheathing or resheathing of the prosthetic valve.

As shown in FIG. 2C, the inner shaft 26 may extend through the threaded rod 36, and the proximal end of the inner shaft may extend through the housing 30 beyond the proximal end 12 thereof. A hemostasis valve 28 attached to the proximal end of the inner shaft 26 (FIG. 1B) may permit removal of air from the device 10 through the inner shaft before deployment of the valve.

The handle housing 30 includes a top portion 30a (FIG. 1A) and a bottom portion 30b (FIG. 2A). The top and bottom portions 30a and 30b may be individual components joined to one another. Collectively, the top and bottom portions 30a and 30b define an elongated space 34 (FIG. 2C) along the longitudinal axis of the housing 30 in which a piston assembly 40 including the threaded rod 36 and proximal and distal piston cylinders 41 and 42 (described below) may be disposed.

The handle housing 30 further defines a pocket 37 that extends transversely through the top portion 30a and bottom portion 30b for receiving a deployment actuator 21. The deployment actuator 21 is internally threaded and is threadedly engaged with the threaded rod 36. The pocket 37 is sized and shaped to receive the deployment actuator 21 with minimal clearance, such that the location of the deployment actuator remains substantially fixed relative to the housing 30 as it is rotated about the threaded rod 36.

Rotation of the deployment actuator 21 in one direction (either clockwise or counterclockwise depending on the orientation of the threads on the threaded rod 36) causes the threaded rod to move proximally within the piston cylinders 41, 42. Similarly, rotation of the deployment actuator 21 in the opposite direction causes the threaded rod 36 to move distally within the piston cylinders 41, 42.

The proximal and distal piston cylinders 41 and 42 together define an enlarged bore 35 (FIG. 2C) that is sized to slidingly receive the threaded rod 36. The enlarged bore 35 has an inner diameter slightly larger than the outer diameter of the threaded rod 36. For example, the enlarged bore 35 may have an inner diameter of about 0.5 inches or about 0.75 inches. Each of the piston cylinders 41, 42 has an open end adjacent the deployment actuator 21 and a closed end remote from the deployment actuator. The enlarged bore 35 preferably permits the threaded rod 36 to travel a distance that is at least as long as the anticipated length of the prosthetic valve to be delivered (e.g., at least about 50 mm), such that the distal sheath 24 can be fully advanced from around the prosthetic valve.

Each of the proximal and distal piston cylinders 41, 42 includes a respective pressure chamber 43, 44 within a portion of the enlarged bore 35. The proximal pressure chamber 43 is defined by the closed end of the proximal piston cylinder 41 and the end surface 38a of the threaded rod 36. A proximal seal 45 (e.g., an o-ring) provides a seal between the unthreaded end 38 of the threaded rod 36 and the inner surface of the proximal piston cylinder 41, thereby preventing leakage from the proximal pressure chamber 43. The proximal seal 45 may be formed contiguously with the proximal surface 38a of the threaded rod 36, or it may be a separate component that extends within a groove around the unthreaded end 38 of the threaded rod. A further seal 47 (e.g., an o-ring) in the closed end of the piston cylinder 41 provides a seal with the inner shaft 26.

The distal pressure chamber 44 is defined by the closed end of the distal piston cylinder 42 and the end surface 39a of the threaded rod 36. A distal seal 46 (e.g., an o-ring) provides a seal between the unthreaded end 39 of the threaded rod 36 and the inner surface of the distal piston cylinder 42, thereby preventing leakage from the distal pressure chamber 44. The distal seal 46 may be formed contiguously with the distal surface 39a of the threaded rod 36, or it may be a separate component that extends within a groove around the unthreaded end 39 of the threaded rod. An additional seal 48 (e.g., an o-ring) in the closed end of the piston cylinder 42 provides a seal with the inner shaft 26.

An outer surface of the inner shaft 26 may be sealed against an inner surface of a lumen extending longitudinally within the threaded rod 36, by a metallic weld, press-fit interference, or by an adhesive extending between the inner shaft and the lumen of the threaded rod, for example. This seal between the inner shaft 26 and the threaded rod 36 prevents leakage between the proximal pressure chamber 43 and the distal pressure chamber 44 through the lumen of the threaded rod.

A pneumatic switch 90 (FIG. 1A) may be in fluid communication with the proximal and distal pressure chambers 43, 44 via lengths of tubing 91, 92. The tubing 91 may extend between the pneumatic switch 90 and a proximal port 93 in the proximal pressure chamber 43, and the tubing 92 may extend between the pneumatic switch and a distal port 94 in the distal pressure chamber 44. The proximal and distal ports 93, 94 may be oriented toward any direction. For example, the proximal port 93 is facing proximally in FIGS. 2A and 2B and distally in FIG. 2C.

The pneumatic switch 90 may be movable to a first position that provides pressurized fluid (e.g., air) from a pressure source (not shown) to the proximal pressure chamber 43, while venting the distal pressure chamber 44 to atmospheric pressure, thereby creating a pressure differential between the proximal and distal pressure chambers. For example, pressurized air can be provided to the proximal pressure chamber 43 at a pressure of about 40 psig to about 50 psig, whereas the pressure in the distal pressure chamber 44 can be reduced to atmospheric pressure.

In other examples, any other pressure differential between the proximal pressure chamber 43 and the distal pressure chamber 44 may be used. It is not required that the distal pressure chamber 44 be vented to atmospheric pressure when the proximal pressure chamber 43 is pressurized, so long as the pressure in the proximal pressure chamber exceeds the pressure in the distal pressure chamber. In one example, the distal pressure chamber 44 may retain a positive pressure of about 10 psig while the proximal pressure chamber 43 is pressurized to a pressure of about 40 psig.

The higher pressure in the proximal pressure chamber 43 relative to the lower pressure in the distal pressure chamber 44 will exert a distal force F1 against the proximal surface 38a of the threaded rod 36. The pressure differential between the pressure chambers 43 and 44 will thus provide an assistive distal force F1 to the threaded rod when the deployment actuator 21 is rotated in a first direction that causes the threaded rod to move distally.

When the proximal pressure chamber 43 is providing an assistive distal force F1 to the threaded rod 36, it preferably will still be necessary to rotate the deployment actuator 21 to effect distal movement of the threaded rod due to the engagement of the threads of the deployment actuator with the threaded rod and the relatively low thread angle (i.e., the threads extend relatively perpendicular to the longitudinal axis of the threaded rod) of the threads of the deployment actuator and those of the threaded rod.

In other embodiments (not shown), higher thread angles may be used. If the thread angle is high enough, it may be possible to effect distal movement of the threaded rod 36 and rotational motion of the deployment actuator 21 solely by creating a pressure differential between the pressure chambers 43 and 44, without a user needing to rotate the deployment actuator manually. In some embodiments (not shown), the threaded coupling between the threaded rod 36 and the deployment actuator 21 may be replaced with another mechanical feature or a friction fit between the rod and the deployment actuator. For example, the threaded rod and internally threaded deployment actuator can be replaced with a toothed rack and a pinion knob, respectively.

The pneumatic switch 90 may also be movable to a second position that provides pressurized fluid (e.g., air)

from the pressure source to the distal pressure chamber 44, while venting the proximal pressure chamber 43 to atmospheric pressure, thereby creating a pressure differential between the distal and proximal pressure chambers. For example, pressurized air can be provided to the distal pressure chamber 44 at a pressure of about 40 psig to about 50 psig, whereas the pressure in the proximal pressure chamber 43 can be reduced to atmospheric pressure.

In other examples, any other pressure differential between the distal pressure chamber 44 and the proximal pressure chamber 43 may be used. It is not required that the proximal pressure chamber 43 be vented to atmospheric pressure when the distal pressure chamber 44 is pressurized, so long as the pressure in the distal pressure chamber exceeds the pressure in the proximal pressure chamber. In one example, the proximal pressure chamber 43 may retain a positive pressure of about 10 psig while the distal pressure chamber 44 is pressurized to a pressure of about 40 psig.

The higher pressure in the distal pressure chamber 44 relative to the lower pressure in the proximal pressure chamber 43 will exert a proximal force F2 against the distal surface 39a of the threaded rod 36. The pressure differential between the pressure chambers 43 and 44 will thus provide an assistive proximal force F2 to the threaded rod when the deployment actuator 21 is rotated in a second direction that causes the threaded rod to move proximally.

When the distal pressure chamber 44 is providing an assistive proximal force F2 to the threaded rod 36, it preferably will still be necessary to rotate the deployment actuator 21 to effect proximal movement of the threaded rod due to the engagement of the threads of the deployment actuator with the threaded rod and the relatively low thread angle (i.e., the threads extend relatively perpendicular to the longitudinal axis of the threaded rod) of the threads of the deployment actuator and those of the threaded rod.

The pneumatic switch 90 may optionally be movable to a third position that vents both the proximal and distal pressure chambers 43, 44 to atmospheric pressure. In this position, there is no pressure differential between the proximal and distal pressure chambers 43, 44, so no assistive proximal or distal force is provided to the threaded rod. This third position may be used when a user wishes to turn off the force-assist feature of the piston assembly 40.

The operating handle 20 may also include a resheathing lock mechanism (not shown) as described, for example, in co-pending U.S. patent application Ser. No. 13/788,820, filed Mar. 7, 2013, the disclosure of which is hereby incorporated by reference herein, for preventing the user from accidentally completing the deployment of a valve located in the compartment 23. Such a resheathing lock may limit the longitudinal movement of the threaded rod 36 within the handle housing 30.

The operation of the present invention to deploy a prosthetic valve will now be described. To load the delivery device 10 with a collapsible prosthetic valve, the user may pressurize the proximal pressure chamber 43 and rotate the deployment actuator 21 in a first direction to move the threaded rod 36 distally, and with it the inner shaft 26, thereby advancing the distal sheath 24 and exposing the compartment 23. A compressed or crimped valve may then be loaded around the support shaft 19, and retention members on the distal end of the valve may be coupled to the recesses 80 in the retainer 25. The user may then pressurize the distal pressure chamber 44 while venting the proximal pressure chamber 43, and may rotate the deployment actuator 21 in a second direction opposite the first direction to move the threaded rod 36 proximally, and with it the inner shaft 26, thereby retracting the distal sheath 24 over the compartment 23 to hold the valve in the compressed state. In this starting condition, the handle 20 will be in an initial state with the threaded rod 36 at its proximalmost position within the enlarged bore 35.

To use the operating handle 20 to deploy a prosthetic valve that has been loaded into the compartment 23 and covered by the distal sheath 24, the user may pressurize the proximal pressure chamber 43 and rotate the deployment actuator 21 in the first direction to move the threaded rod 36 and the inner shaft 26 distally within the enlarged bore 35, which thereby pushes the distal sheath distally relative to the compartment and exposes and initiates deployment of the valve located therein. After movement of the distal sheath 24 has partially revealed the compartment 23, the user may continue the deployment process by continuing to rotate the deployment actuator 21 to move the threaded rod 36 and the inner shaft 26 further distally, which is still being assisted by the pressurized proximal pressure chamber 43.

While the outer sheath 24 is uncovering the compartment 23 to expand the prosthetic valve therein, the user can evaluate the position of the valve relative to the patient's aortic annulus and may be able to determine whether the valve is functioning properly. If repositioning or removal is desired before the valve is fully uncovered, the user may resheathe the valve by pressurizing the distal pressure chamber 44 while venting the proximal pressure chamber 43, and rotating the deployment actuator 21 in the direction opposite that used for deployment. Such rotation and a proximal force assist from the distal pressure chamber 44 will cause the threaded rod 36 to progress proximally through the deployment actuator 21 until the threaded rod has reached the starting position shown in FIG. 2A, thereby recollapsing the expanded part of the valve as the distal sheath 24 is moved proximally over the compartment 23. With the valve resheathed, the user may reposition the delivery device 10 and may commence the deployment procedure once again or may simply remove the valve from the patient.

Although not shown in the figures, it will be appreciated that the device 10 may include a resheathing lock as described, for example, in co-pending U.S. patent application Ser. No. 13/788,820, filed Mar. 7, 2013, or other structures for selectively limiting the movement of the threaded rod 36 within the handle housing. The resheathing lock of the device 10 will limit the movement of the threaded rod 36 distally within the housing to prevent the user from completing the deployment of a prosthetic valve unintentionally.

Once the proper positioning of the valve relative to the aortic annulus has been assured, the user may complete the deployment process. The deployment operation may be completed by continuing to translate the threaded rod 36 distally by rotating the deployment actuator 21 with a distal force assist from the proximal pressure chamber 43 until the valve is fully uncovered. When the valve has been completely unsheathed, the stent portion of the valve self-expands and disengages from the retainer 25, thereby releasing the valve from the catheter assembly 16.

In a variation of the device 10, the operating handle 20 may be provided with only a single pressure chamber. Typically, the highest force encountered by a user while rotating the deployment actuator 21 is during resheathing of a partially-deployed prosthetic valve. In the transapical device 10, a proximal force assist F2 can be provided by the distal pressure chamber 44 to the threaded rod 36 during rotation of the deployment actuator 21 to translate the threaded rod in a proximal direction during reseheathing. In this device 10, the proximal pressure chamber 43 can be omitted, such that no distal force assist F1 is provided during rotation of the deployment actuator 21 to translate the threaded rod in a distal direction.

Figure 3A:
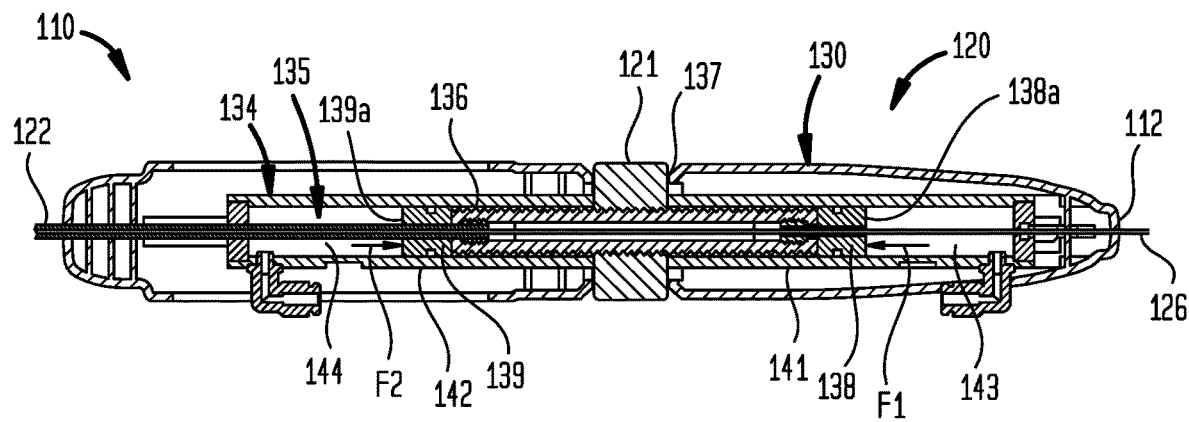
FIG. 3A is a longitudinal cross-section of an operating handle for a transfemoral delivery device for a collapsible prosthetic heart valve.
Figure 3B:
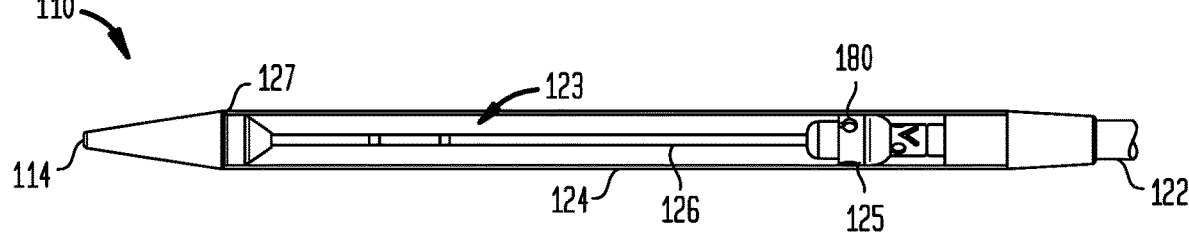
FIG. 3B is a top view of the distal portion of a transfemoral catheter assembly that may be operated by the operating handle of FIG. 3A, the distal sheath of the assembly being partially removed to show the interior thereof.
Figure 4A:
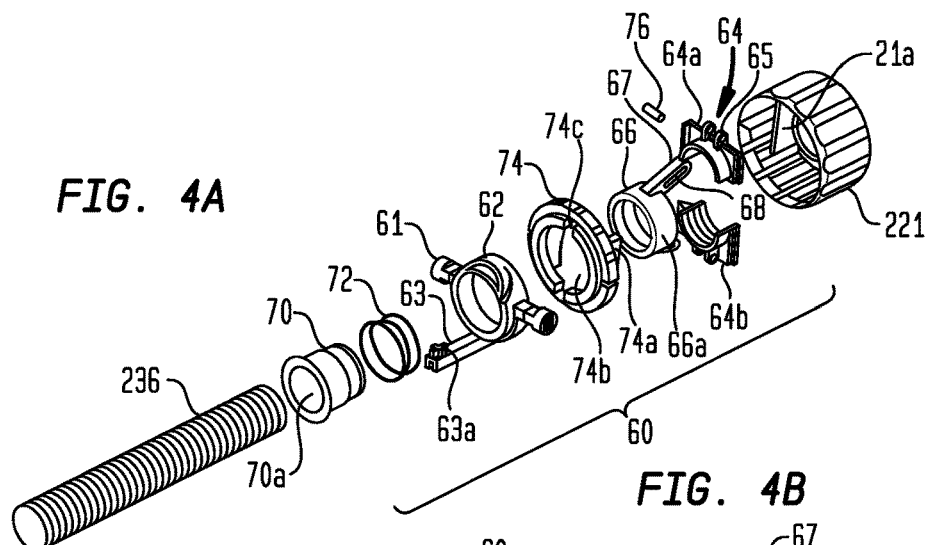
FIG. 4A is an exploded perspective view of a deployment actuator assembly that can be integrated into the operating handle of FIG. 1A or FIG. 3A.
Figure 4B:
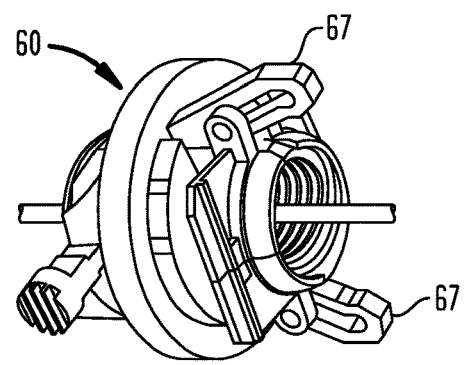
FIG. 4B is an enlarged perspective view of a portion of the deployment actuator assembly of FIG. 4A.
Figure 4C:
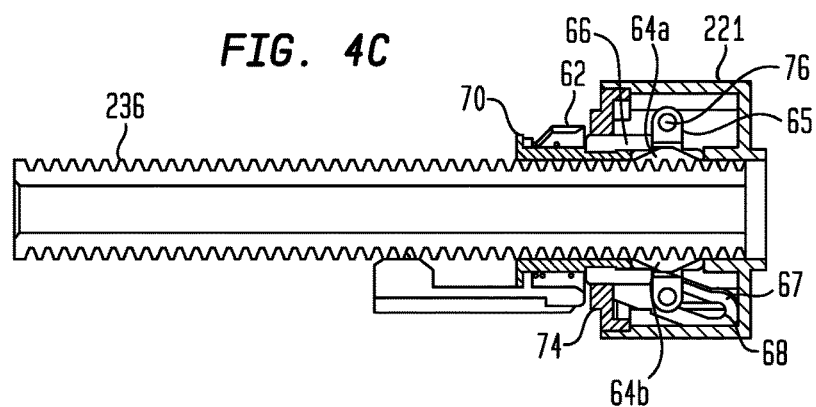
FIG. 4C is a longitudinal cross-section of the deployment actuator assembly of FIG. 4A, with the deployment actuator shown in threaded engagement with the threaded rod.
Figure 4D:
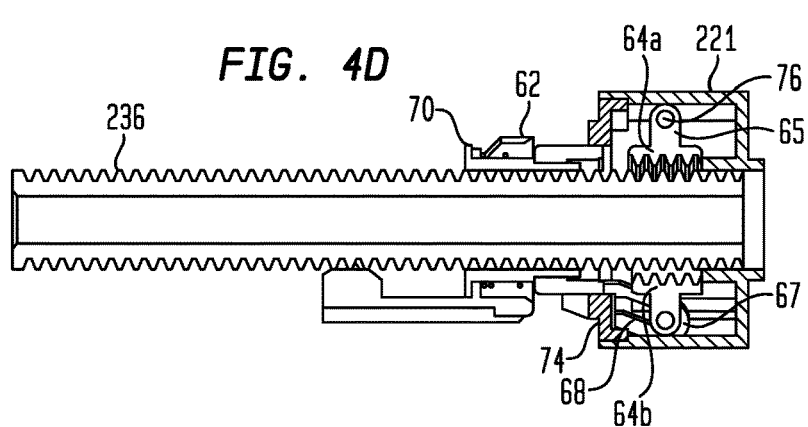
FIG. 4D is a longitudinal cross-section of the deployment actuator assembly of FIG. 4A, with the deployment actuator shown disengaged from the threaded rod.

Referring now to FIGS. 3A and 3B, an exemplary transfemoral delivery device 110 for a collapsible prosthetic heart valve (or other types of self-expanding collapsible stents) has a catheter assembly 116 for delivering the heart valve to and deploying the heart valve at a target location, and an operating handle 120 for controlling deployment of the valve from the catheter assembly. The delivery device 110 extends from a proximal end 112 to an atraumatic tip 114 at the distal end of the catheter assembly 116. The atraumatic tip 114 may be formed from or may include a radiopaque material to enable the tip to be visible under fluoroscopy during a deployment procedure. The catheter assembly 116 is adapted to receive a collapsible prosthetic heart valve (not shown) in a compartment 123 defined between an inner shaft 126 and a distal sheath 124.

The inner shaft 126 may extend through the operating handle 120 to the atraumatic tip 114 of the delivery device, and includes a retainer 125 affixed thereto at a spaced distance from tip 114 and adapted to hold a collapsible prosthetic valve in the compartment 123. The inner shaft 126 may be made of a flexible material such as braided polyimide or polyetheretherketone (PEEK), for example. Using a material such as PEEK may improve the resistance of the inner shaft 126 to kinking while the catheter assembly 116 is tracking through the vasculature of a patient. The retainer 125 may have recesses 180 therein that are adapted to hold corresponding retention members of the valve.

The distal sheath 124 surrounds the inner shaft 126 and is slidable relative to the inner shaft such that it can selectively cover or uncover the compartment 123. The distal sheath 124 is affixed at its proximal end to an outer shaft 122, the proximal end of which is connected to the operating handle 120 in a manner to be described. The distal end 127 of the distal sheath 124 abuts the atraumatic tip 114 when the distal sheath is fully covering the compartment 123, and is spaced apart from the atraumatic tip when the compartment is at least partially uncovered.

The operating handle 120 is adapted to control deployment of a prosthetic valve located in the compartment 123 by permitting a user to selectively slide the outer shaft 122 and the attached distal sheath 124 proximally or distally relative to the inner shaft 126, thereby respectively uncovering or covering the compartment with the distal sheath. The outer shaft 122 may be made of a flexible material such as nylon 11 or nylon 12, and it may have a round braid construction (i.e., round cross-section fibers braided together) or flat braid construction (i.e., rectangular cross-section fibers braided together), for example.

The proximal end of the inner shaft 126 may be connected in substantially fixed relationship to an outer housing 130 of the operating handle 120, and the proximal end of the outer shaft 122 may be affixed to a threaded rod 136 that is translatable along a longitudinal axis of the handle housing. This structure enables a user to selectively slide the outer shaft 122 relative to the inner shaft 126 by translating the threaded rod 136 relative to the housing 130. A hemostasis valve (not shown) may include an internal gasket adapted to create a seal between the inner shaft 126 and the proximal end of the outer shaft 122. The threaded rod 136 has an unthreaded proximal end 138 with an end surface 138*a*, and an unthreaded distal end 139 with an end surface 139*a*. Similar to the threaded rod 36, the threaded rod 136 preferably is longer than the anticipated maximum travel distance of the distal sheath 124.

The handle housing 130 may include a top portion and a bottom portion. The top portion and bottom portion may be similar to the top and bottom portions 30*a* and 30*b* described above. The handle housing 130 defines an elongated space 134 along the longitudinal axis of the housing in which a piston assembly 140 including the threaded rod 136 and proximal and distal piston cylinders 141 and 142 (described below) may be disposed.

The handle housing 130 further defines a pocket 137 that extends transversely through the housing 130 for receiving a deployment actuator 121. The deployment actuator 121 is internally threaded and is in threaded engagement with the threaded rod 136. The pocket 137 is sized and shaped to receive the deployment actuator 121 with minimal clearance, such that the location of the deployment actuator remains substantially fixed relative to the housing 130 as it is rotated about the threaded rod 136. Rotation of the deployment actuator 121 produces linear movement of the threaded rod 136 in the same way as described above with reference to the deployment actuator 21 and the threaded rod 36.

The proximal and distal piston cylinders 141 and 142 together define an enlarged bore 135 that is sized to slidingly receive the threaded rod 136. The enlarged bore 135 has an inner diameter slightly larger than the outer diameter of the threaded rod 136. The enlarged bore 135 preferably permits the threaded rod 136 to travel a distance that is at least as long as the anticipated length of the prosthetic valve to be delivered (e.g., at least about 50 mm), such that the distal sheath 124 can be fully retracted from around the prosthetic valve.

Each of the proximal and distal piston cylinders 141, 142 includes a respective pressure chamber 143, 144 within a portion of the enlarged bore 135. The configuration of the proximal and distal pressure chambers 143 and 144 and the structure with which the pressure chambers may provide an assistive distal force F1 or an assistive proximal force F2 to the threaded rod 136 may be the same as described above with respect to the proximal and distal pressure chambers 43 and 44 and the threaded rod 36.

The operating handle 120 may also include a resheathing lock mechanism (not shown) for preventing the user from accidentally completing the deployment of a valve located in the compartment 123, as described above with reference to the operating handle 20.

The operation of the operating handle 120 to deploy a prosthetic valve from the compartment 123 is similar to the operation of the operating handle 20 of the device 10 described above. The user can pressurize the distal pressure chamber 144 and rotate the deployment actuator 121 in a first direction to translate the threaded rod 136 proximally within the enlarged bore 135, and with it the outer shaft 122, which thereby retracts the distal sheath 124 proximally from the compartment 123 and exposes and initiates deployment of the valve located therein.

After movement of the distal sheath 124 has partially revealed the compartment 123, the user may continue the deployment process by continuing to rotate the deployment actuator 121 with a proximal force assist from the distal pressure chamber 144, moving the threaded rod 136 further proximally within the enlarged bore 135, and moving the outer shaft 122 and the distal sheath further proximally.

If the user desires to resheathe and reposition the valve or remove the valve from the patient before full deployment, the user can do so by pressurizing the proximal pressure chamber 143 while venting the distal pressure chamber 144, and rotating the deployment actuator 121 in the direction opposite that used for deployment. Such rotation and a distal force assist from the proximal pressure chamber 143 will cause the threaded rod 136 to progress distally through the deployment actuator 121 until the threaded rod has reached the starting position, thereby recollapsing the expanded part of the valve as the distal sheath 124 is moved distally over the compartment 123. With the valve resheathed, the user may reposition the delivery device 110 and commence the deployment procedure once again or can remove the valve from the patient.

Although not shown in the figures, it will be appreciated that the device 110 may include a resheathing lock as described, for example, in co-pending U.S. patent application Ser. No. 13/788,820, filed Mar. 7, 2013, or other structures for selectively limiting the movement of the threaded rod 136 within the handle housing.

Once the proper positioning of the valve has been assured, the deployment operation may be completed by continuing to translate the threaded rod 136 proximally by rotating the deployment actuator 121 with a proximal force assist from the distal pressure chamber 144 until the valve is fully deployed.

In a variation of the device 110, the operating handle 120 may be provided with only a single pressure chamber. Typically, the highest force encountered by a user while rotating the deployment actuator 121 is during resheathing of a partially-deployed prosthetic valve. In the transfemoral device 110, a distal force assist F1 can be provided by the proximal pressure chamber 143 to the threaded rod 136 during rotation of the deployment actuator 121 to translate the threaded rod in a distal direction during resehathing. In this device 110, the distal pressure chamber 144 can be omitted, such that no proximal force assist F2 is provided during rotation of the deployment actuator 121 to translate the threaded rod in a proximal direction to deploy the valve.

Many modifications to the various features of the delivery devices described herein are possible. For example, referring to FIGS. 4A-4D, either of the devices 10 or 110 may include a coupling assembly 60 to selectively place the deployment actuator 21 or 121 in threaded engagement with the threaded rod 36 or 136. Rotational motion of the deployment actuator is only converted into linear motion of the threaded rod when the coupling assembly 60 engages the deployment actuator with the threaded rod.

The ability of the coupling assembly 60 to translate rotation of the deployment actuator 221 into translation of the threaded rod 236 relative to the housing 30 or 130 may provide the user with the ability to carefully control movement of the threaded rod both proximally within the enlarged bore 35 during a valve deployment operation, and distally during a resheathing operation (for the transapical device 10), or both distally within the enlarged bore 135 during a valve deployment operation, and proximally during a resheathing operation (for the transfemoral device 110). The ability of the coupling assembly 60 to decouple the deployment actuator 221 from the threaded rod 236 so that the carriage assembly can freely move longitudinally relative to the housing 30 or 130 enables gross movement of the threaded rod proximally or distally within the enlarged bore without the mechanical advantage provided by the deployment actuator.

Such gross movement of the threaded rod 236 can be provided by either: (1) the user actuating the pneumatic switch 90 to either pressurize the proximal pressure chamber 43 or 143 to move the threaded rod distally or to pressurize the distal pressure chamber 44 or 144 to move the threaded rod proximally; or (2) the user manually sliding the threaded rod 236 proximally or distally by grasping and sliding a tab or button fixedly coupled to the threaded rod (an example of such a tab or button is shown in the aforementioned U.S. patent application Ser. No. 13/788,820).

The coupling assembly 60 may be integrated into either the handle 20 or the handle 120 described above by replacing the deployment actuator 21 or 121 with the deployment actuator 221 and by separating the proximal and distal piston cylinders 41, 42 or 141, 142 from one another along the longitudinal axis of the handle to create enough room to accommodate the coupling assembly. The threaded rod 236 may need to be longer than the threaded rod 36 or 136 to accommodate the coupling assembly 60 thereon while still providing sufficient travel distance to completely deploy a prosthetic valve.

The coupling assembly 60 may include a split nut 64 mounted within the deployment actuator 221 through an open side thereof. The split nut 64 has first and second nut portions 64a and 64b that are internally threaded to mate with the threaded rod 236. Each nut portion 64a and 64b has a pair of spaced tabs projecting therefrom, with each tab having an aperture 65 sized to receive a pin 76.

A nut ramp 66 may be mounted within the deployment actuator 221 adjacent the split nut 64. The nut ramp 66 has an annular body 66a with a pair of cam arms 67 projecting proximally therefrom and slidably positioned between the spaced tabs on respective nut portions 64a and 64b. Each cam arm 67 has an elongated cam slot 68 sized to slidably receive the pin 76 therein.

A retention ring 74 may be press fit into the open side of the deployment actuator 221. A plurality of ribs on the outer periphery of the retention ring 74 may mate with a plurality of recesses formed on the inner surface of the deployment actuator 221 to prevent the retention ring from rotating relative to the deployment actuator. The retention ring 74 may include a pair of spaced flanges 74a that cooperate with similar spaced flanges formed on the interior of the deployment actuator 221 to sandwich the generally rectangular outer periphery of the split nut 64 in an assembled position. A large central aperture 74b in the retention ring 74 is sized to slidably receive the annular body 66a of the nut ramp 66 therethrough. The retention ring 74 further includes a pair of diametrically opposed slots 74c that are sized and positioned to receive the cam arms 67 of the nut ramp 66 as the annular body 66a thereof travels through the aperture 74b in the retention ring.

A ring 62 may be positioned adjacent the retention ring 74 and may be coupled to the nut ramp 66 by a flanged fastening ring 70 that fits through the ring 62 and snaps into the nut ramp with an interference fit. The connection between the fastening ring 70 and the nut ramp 66 is such that the ring 62 has some freedom of movement between the annular body 66a of the nut ramp and the flange of the fastening ring. An aperture 70a extending longitudinally through the fastening ring 70 has a diameter that is larger than the diameter of the threaded rod 236 so that the threaded rod can slide smoothly and freely therethrough. A compression spring 72, the purpose of which will be described below, may be mounted in the annular space between the fastening ring 70 and the ring 62 and may be constrained longitudinally between the annular body 66a of the nut ramp 66 and an annular flange formed on the ring 62.

A pair of buttons 61 positioned on opposite lateral sides of the ring 62 may be slidably received in longitudinal openings (not shown) formed on opposite lateral sides of the housing 30 or 130. Movement of the buttons 61 to a proximal position in the openings will cause the ring 62 and, hence, the nut ramp 66 to move proximally relative to the split nut 64, and movement of the buttons 61 to a distal position in the openings will cause the ring 62 and the nut ring 66 to move distally relative to the split nut.

The ring 62 further includes an arm 63 that extends distally from an outer periphery of the ring. The arm 63 is sized to reside between a pair of posts (not shown) that may project upwardly from the bottom housing portion. The free end of the arm 63 includes a pair of nubs 63*a* that project therefrom in opposite lateral directions. When the buttons 61 are moved to a distalmost position in the housing openings, the nubs 63*a* will be positioned on a distal side of the posts, locking the ring 62 in this position. When the buttons 61 are moved to a proximalmost position in the housing openings, the nubs 63*a* will be positioned on the proximal side of the posts, locking the ring in this position. As the buttons 61 are moved between the proximalmost and distalmost positions, the nubs 63*a* will deflect the posts slightly outward as they move between the posts.

The first and second nut portions 64*a* and 64*b* have freedom of motion to slide in a substantially perpendicular direction towards or away from the threaded rod 236, but they are constrained from longitudinal movement relative to the threaded rod by the sandwiching effect of the inner flanges 21*a* of the deployment actuator 221 and the retention ring flanges 74*a*. Thus, in the assembly described above, the cam slots 68 are adapted to translate movement of the nut ramp 66 along the longitudinal axis into lateral movement of the first and second nut portions 64*a* and 64*b* towards or away from the threaded rod 236.

For example, when the buttons 61 are moved to the proximal ends of the respective housing openings, the pins 76 will be disposed at the distal ends of the cam slots 68, which are located closest to the threaded rod 236 in a direction perpendicular to the longitudinal axis. In this position, the nut portions 64*a* and 64*b* will be in threaded engagement with the threaded rod 236. When the buttons 61 are moved to the distal ends of the respective housing openings, the pins 76 will be disposed at the proximal ends of the cam slots 68, which are located farthest from the threaded rod 236 in the direction perpendicular to the longitudinal axis. In this position, the nut portions 64*a* and 64*b* will be disengaged from the threaded rod 236. Therefore, when a user slides the buttons 61 proximally, rotation of the deployment actuator 221 translates the threaded rod 236, and when the user slides the buttons distally, the deployment actuator becomes decoupled from the threaded rod.

When the user slides the buttons 61 proximally to move the nut portions 64*a* and 64*b* toward the threaded rod 236, interference between the threads on the nut portions and the threads on the threaded rod may prevent complete threaded engagement between the split nut 64 and the threaded rod. Nonetheless, the ring 62 will move to its proximalmost position so that the nubs 63*a* snap into place on the proximal side of the posts. With the aforementioned interference preventing the nut portions 64*a* and 64*b* from continuing into full threaded engagement with the threaded rod 236, and thus preventing the nut ramp 66 from further movement proximally, the last portion of the movement of the ring 62 in the proximal direction will cause the spring 72 to compress. This compression will add an extra lateral force to the nut ramp 66. Accordingly, as the deployment actuator 221 is rotated, the threads of the nut portions 64*a* and 64*b* will properly align with the threads of threaded rod 236 and the biasing force exerted by the spring 72 on the nut ramp 66 will assure that the nut portions become fully engaged with the threaded rod.

In another variation, referring to FIGS. 5A-5D, either of the devices 10 or 110 may replace the deployment actuator 21 or 121 and the pneumatic switch 90 with a smart wheel assembly 300, which is adapted to combine the control of both the sliding of the threaded rod and the provision of pressurized fluid to the proximal and distal pressure chambers in a single assembly. Similar to the coupling assembly 60, the smart wheel assembly 300 may be integrated into either the handle 20 or the handle 120 described above by separating the proximal and distal piston cylinders 41, 42 or 141, 142 from one another along the longitudinal axis of the handle to create enough room to accommodate the smart wheel assembly.

The smart wheel assembly 300 includes a deployment actuator 321 and a toggle guide 390. The toggle guide 390 is adapted to translate in a longitudinal direction of the operating handle in response to rotation of the deployment actuator 321, thereby actuating a pneumatic switch (not shown) that provides pressurized fluid to either the proximal or distal pressure chamber, depending on the position of the toggle guide. For example, the smart wheel assembly 300 has a contracted condition with a width W1 when the toggle guide 390 is disposed immediately adjacent the deployment actuator 321, as shown in FIG. 5B. In this contracted condition, the distal pressure chamber may be pressurized. The smart wheel assembly 300 also has an expanded condition with a width W2 when the toggle guide is remote from the deployment actuator (position 390' in FIG. 5B). In this expanded condition, the proximal pressure chamber may be pressurized.

The deployment actuator 321 is internally threaded, and when assembled into the handle 20 or 120, is in threaded engagement with the threaded rod 36 or 136. The toggle guide 390 has an inner bore 350 that is adapted to slidably receive the threaded rod 36 or 136 therethrough.

The substantially flat face of the deployment actuator 321 facing the toggle guide 390 has an outer ratchet surface 322 in the form of a ring extending around the outer circumference of the surface, and an inner ratchet surface 323 in the form of a ring disposed radially inward of the outer ratchet surface. The outer ratchet surface 322 and the inner ratchet surface 323 each have a plurality of teeth 324. The teeth 324 of the outer ratchet surface 322 are angled in the opposite direction of those of the inner ratchet surface 323.

The smart wheel assembly 300 has an outer cylinder 332 disposed radially inside the toggle guide 390, the outer cylinder having a ratchet surface formed by a plurality of teeth 334 facing the outer ratchet surface 322 of the deployment actuator 321. The smart wheel assembly 300 also has an inner cylinder 333 disposed radially inside the outer cylinder 332, the inner cylinder having a ratchet surface formed by a plurality of teeth 334 facing the inner ratchet surface 323 of the deployment actuator 321. The teeth 334 of the outer cylinder 332 are angled in the opposite direction of those of the inner ratchet 333 cylinder.

The outer cylinder 332 is arranged such that its teeth 334 confront and are adapted to mesh with the teeth 324 of the outer ratchet surface 322 when the deployment actuator 321 is rotated in a first direction R1 (FIG. 5C), such that when engaged with one another, rotation of the deployment actuator in the first direction causes the outer cylinder to rotate therewith, while rotation of the deployment actuator in a second direction R2 opposite the first direction does not rotate the outer cylinder.

The inner cylinder 333 is arranged such that its teeth 334 confront and are adapted to mesh with the teeth 324 of the inner ratchet surface 323 when the deployment actuator 321 is rotated in the second direction R2, such that when engaged with one another, rotation of the deployment actuator in the second direction causes the inner cylinder to rotate therewith, while rotation of the deployment actuator in the first direction R1 does not rotate the inner cylinder.

The smart wheel assembly 300 has an outer spring 342 extending between the outer cylinder 332 and an inner end surface 391 of the toggle guide 390, and an inner spring 343 extending between the inner cylinder 333 and the inner end surface of the toggle guide. The springs 342 and 343 are always under compression, such that their biasing force will tend to urge the toggle guide 390 away from the deployment actuator 321, thereby urging the smart wheel assembly 300 toward the expanded condition. The toggle guide 390 has separation fins 355 that are adapted to maintain the positions of the ratchet cylinders 332, 333 and the springs 342, 343 relative to the deployment actuator 321 as the smart wheel assembly 300 moves between the contracted and expanded conditions.

The toggle guide 390 has a guide slot 360 disposed in the inner separation fin 355. The guide slot 360 has a first end 361 adjacent the deployment actuator 321 and a second end 362 remote from the deployment actuator. The second end 362 of the guide slot 360 has a ledge portion 363 extending substantially perpendicularly to a longitudinal axis L of the smart wheel assembly 300. The guide slot 360 is sized to accommodate a pin 365 extending radially inward from an inner surface of the inner cylinder 333. The guide slot 360 and the pin 365 are configured so that the toggle guide 390 can move along the longitudinal axis L a distance T (FIG. 5B) as the pin 365 moves between the first and second ends 361, 362 of the guide slot.

The guide slot 360 and the pin 365 are configured such that, when the deployment actuator 321 is at rest and the pin is disposed adjacent the first end of 361 of the guide slot 360, the biasing force of the springs 342, 343 will keep the toggle guide 390 at the position 390' (FIG. 5B), with the smart wheel assembly being in the expanded condition with a width W2. When the deployment actuator 321 is rotated in the second direction R2, which also rotates the inner cylinder 333 in the second direction, the pin 365 will move along the guide slot 360 to the second end 362 and onto the ledge portion 363 of the guide slot, thereby further compressing the springs 342, 343 and disposing the toggle guide 390 adjacent the deployment actuator 321 as shown in FIG. 5B, such that the smart wheel assembly is in the contracted condition with a width W1 smaller than the width W2.

The guide slot 360 and the pin 365 are also configured such that, when deployment actuator 321 is at rest and the pin 365 is disposed at the second end 362 of the guide slot 360, friction between the pin and the ledge portion 363 of the guide slot will be sufficient to prevent the biasing force of the springs 342, 343 from pushing the toggle guide 390 back to the position 390'. When the deployment actuator 321 is rotated in the first direction R1, there will be friction between the inner cylinder 333 and the deployment actuator as the opposing teeth slip past one another, and this friction force will slightly rotate the inner cylinder relative to the toggle guide to a degree that is sufficient to overcome the friction between the pin 365 and the ledge portion 363 of the guide slot 360, so that the biasing force of the springs 342, 343 will move the toggle guide 390 to the position 390', such that the smart wheel assembly is disposed in the expanded condition.

In use with the transapical delivery device 10, for example, when the smart wheel assembly 300 is at rest with the pin 365 at the first end 361 of the guide slot 360, the smart wheel assembly will be disposed in the expanded condition with the toggle guide remote from the deployment actuator (position 390') and the proximal pressure chamber 43 may be pressurized, thereby providing a distal force to the threaded rod 36.

When a user desires to begin advancing the distal sheath 24 distally to begin deployment of a prosthetic valve, the user may rotate the deployment actuator 321 in the first direction R1, which will rotate the outer cylinder 332 therewith in the first direction R1, and which will move the threaded rod 36 distally through the inner bore 350 of the toggle guide 390 with a distal pressure assisting force from the pressurized proximal pressure chamber 43. The toggle guide 390 and the inner cylinder 333 will not rotate with the deployment actuator, because the teeth 334 of the inner cylinder are not engaged with the teeth 324 of the deployment actuator 321.

If a user desires to retract the distal sheath 24 proximally to resheathe the prosthetic valve, the user may begin to rotate the deployment actuator 321 in the second direction R2, which will rotate the inner cylinder 333 therewith in the second direction R2, thereby sliding the pin 365 along the guide slot 360 to the second end 362 and onto the ledge portion 363 of the guide slot, drawing the toggle guide 390 toward the deployment actuator 321 while further compressing the springs 342, 343 as shown in FIG. 5B, such that the smart wheel assembly is disposed in the contracted condition.

During this movement of the pin 365 from the first end 361 to the second end 362 of the guide slot 360, which may be during approximately 1/10 of a full rotation of the deployment actuator 321 in the second direction R2, the toggle guide 390 and the outer cylinder 333 will not rotate with the deployment actuator, because the teeth 334 of the outer cylinder are not engaged with the teeth 324 of the deployment actuator.

When the toggle guide 390 moves adjacent the deployment actuator 321, a pneumatic switch (not shown) is actuated so that pressurized fluid is provided to the distal pressure chamber 44, while the proximal pressure chamber 43 is vented to atmospheric pressure, thereby providing a proximal force to the threaded rod 36.

When the user continues to rotate the deployment actuator in the second direction R2 with the pin 365 at the second end 362 of the guide slot 360, the resulting continued rotation of the inner cylinder 333 will rotate the toggle guide 390 therewith by way of the pin providing a rotating force to the second end of the guide slot. Also, the continued rotation of the deployment actuator 321 in the second direction R2 will move the threaded rod 36 proximally through the inner bore 350 of the toggle guide 390 with a proximal assisting force from the pressurized distal pressure chamber 44.

If a user desires to resume advancing the distal sheath 24, the user may rotate the deployment actuator 321 in the first direction R1, which will rotate the outer cylinder 332 therewith in the first direction R1. Although the toggle guide 390 and the inner cylinder 333 will not fully rotate with the deployment actuator, because the teeth 334 of the inner cylinder are not engaged with the teeth 324 of the deployment actuator 321, there will be some friction between the teeth 334 of the inner cylinder and the teeth 324 of the deployment actuator as the opposing teeth slip past one another, and this friction force will slightly rotate the inner cylinder relative to the toggle guide to a degree that is sufficient to overcome the friction between the pin 365 and the ledge portion 363 of the guide slot 360, so that the biasing force of the springs 342, 343 will dispose the toggle guide 390 at the position 390' (FIG. 5B) with the pin 365 again adjacent the first end 361 of the guide slot 360, such that the smart wheel assembly is disposed in the expanded condition.

When the toggle guide 390 moves to the position 390' remote from the deployment actuator 321, the pneumatic switch (not shown) is again actuated so that pressurized fluid is provided to the proximal pressure chamber 43, while the distal pressure chamber 44 is vented to atmospheric pressure, thereby providing a distal force to the threaded rod 36, which will permit the user to resume advancing the distal sheath 24 by rotating the deployment actuator in the first direction R1 with a distal pressure assisting force from the pressurized proximal pressure chamber.

The operating handles described herein may be provided with a deployment locking mechanism. Such a deployment locking mechanism may prevent the accidental initiation of deployment by fixing the threaded rod 36 or 136 to the handle housing while the lock is in a locked position. Such a deployment lock may have a structure similar to the deployment locks shown and described in co-pending U.S. patent application Ser. No. 13/212,442, filed Aug. 18, 2011, the disclosure of which is hereby incorporated by reference herein.

Although the operating handles described herein are described as having a piston in the form of a threaded rod 36, 136, or 236, the piston may take other forms. For example, the threaded rod and internally threaded deployment actuator can be replaced with a toothed rack and a pinion knob, respectively. In such an embodiment, the toothed rack may extend into the enlarged bore of the piston cylinders, and it may be sealed against inner surfaces of the piston cylinders by proximal and distal seals, thereby creating proximal and distal pressure chambers extending between the inner surface of each piston cylinder and the seals of the toothed rack.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims. It will be appreciated that the various dependent claims and the features set forth therein can be combined in different ways than presented in the initial claims. It will also be appreciated that the features described in connection with individual embodiments may be shared with others of the described embodiments.

The invention claimed is:

1. A method of delivering a collapsible prosthetic heart valve in a patient, the method comprising:
providing a delivery device having a catheter assembly and an operating handle, the catheter assembly including a compartment adapted to receive the valve in an assembled condition, the operating handle including a housing defining a movement space therein, a piston cylinder disposed within the movement space, a piston slidable in first and second longitudinal directions within the piston cylinder, the piston and the piston cylinder together defining at least one pressure chamber, a deployment actuator coupled to the housing, the deployment actuator being a knob rotatable relative to the housing about a central axis that extends parallel to the first and second longitudinal directions, and a pneumatic switch in fluid communication with the pressure chamber;
loading the valve into the compartment of the catheter assembly and covering the compartment and the valve with a distal sheath of the catheter assembly;
inserting the catheter assembly into the patient so that the valve is positioned at a target location within the patient;
actuating the pneumatic switch, thereby providing a pressurized fluid to the pressure chamber and applying a force to the piston in the first longitudinal direction; and
opening or closing the compartment by rotating the deployment actuator to move the piston of the operating handle in the first longitudinal direction.

2. The method of claim 1, wherein the piston cylinder includes a proximal piston cylinder and a distal piston cylinder, the piston and the proximal piston cylinder together defining a proximal pressure chamber and the piston and the distal piston cylinder together defining a distal pressure chamber, and
wherein the step of opening or closing the compartment comprises opening the compartment by rotating the deployment actuator in a first rotational direction to move the piston of the operating handle in the first longitudinal direction, the method further comprising:
actuating the pneumatic switch, thereby providing a pressurized fluid to the distal chamber and applying a force to the piston in the second longitudinal direction; and
closing the compartment by rotating the deployment actuator in a second rotational direction to move the piston of the operating handle in the second longitudinal direction.

3. The method of claim 1, wherein the catheter assembly further includes a first shaft around which the compartment is defined and an outer shaft connecting the housing to the compartment and at least partially surrounding the first shaft, the first shaft and the distal sheath are operatively connected to the piston, the piston cylinder is a distal piston cylinder surrounding a distal end of the piston, and the step of actuating the pneumatic switch provides a pressurized fluid to the pressure chamber and applies a force to the piston in the second longitudinal direction.

4. The method of claim 1, wherein the catheter assembly further includes a first shaft around which the compartment is defined and an outer shaft at least partially surrounding the first shaft, the first shaft is fixedly connected to the housing, the distal sheath is operatively connected to the piston, and the piston cylinder is a proximal piston cylinder surrounding a proximal end of the piston.

5. The method of claim 1, wherein the piston is a threaded rod in threaded engagement with the deployment actuator, and the deployment actuator is longitudinally constrained relative to the housing.

6. The method of claim 1, wherein the actuating of the pneumatic switch to provide the pressurized fluid to the pressure chamber is effected by rotation of the deployment actuator in a first rotational direction.

7. The method of claim 6, wherein the operating handle further includes a toggle guide moveable in the first and second longitudinal directions relative to the deployment actuator, and the rotation of the deployment actuator in the first rotational direction causes movement of the toggle guide in the first longitudinal direction away from the deployment actuator, thereby actuating the pneumatic switch.

8. The method of claim 1, wherein the target location is the native aortic annulus of the patient.

9. The method of claim 1, wherein the inserting step includes inserting the distal sheath of the catheter assembly through the apex of the heart of the patient.

10. The method of claim 1, wherein the inserting step includes inserting the distal sheath of the catheter assembly through a femoral artery of the patient.

11. A method of delivering a collapsible prosthetic heart valve in a patient, the method comprising:

providing a delivery device having a catheter assembly and an operating handle, the catheter assembly including a compartment adapted to receive the valve in an assembled condition, the operating handle including a housing defining a movement space therein, a piston cylinder disposed within the movement space, a piston slidable in first and second longitudinal directions within the piston cylinder, the piston and the piston cylinder together defining at least one pressure chamber, a deployment actuator coupled to the housing and rotatable relative to the housing, and a pneumatic switch in fluid communication with the pressure chamber, the piston being a threaded rod in threaded engagement with the deployment actuator and the deployment actuator being longitudinally constrained relative to the housing;

loading the valve into the compartment of the catheter assembly and covering the compartment and the valve with a distal sheath of the catheter assembly;

inserting the catheter assembly into the patient so that the valve is positioned at a target location within the patient;

actuating the pneumatic switch, thereby providing a pressurized fluid to the pressure chamber and applying a force to the piston in the first longitudinal direction; and opening or closing the compartment by rotating the deployment actuator to move the piston of the operating handle in the first longitudinal direction.

* * * * *